(12) United States Patent
Berz

(10) Patent No.: US 12,318,228 B2
(45) Date of Patent: *Jun. 3, 2025

(54) METHOD AND APPARATUS FOR MONITORING DEVELOPMENT OF MEDICATION INDUCED SIDE EFFECTS

(71) Applicant: ALACRITY PATIENT SERVICES, INC., San Francisco, CA (US)

(72) Inventor: David Berz, Los Angeles, CA (US)

(73) Assignee: ALACRITY PATIENT SERVICES, INC., San Francisco, CA (US)

( * ) Notice: Subject to any disclaimer, the term of this patent is extended or adjusted under 35 U.S.C. 154(b) by 1010 days.

This patent is subject to a terminal disclaimer.

(21) Appl. No.: 17/360,522

(22) Filed: Jun. 28, 2021

(65) Prior Publication Data
US 2021/0321957 A1    Oct. 21, 2021

Related U.S. Application Data

(63) Continuation-in-part of application No. 16/436,035, filed on Jun. 10, 2019, now Pat. No. 11,045,149, (Continued)

(51) Int. Cl.
*A61B 5/00* (2006.01)
*A61B 5/02* (2006.01)
(Continued)

(52) U.S. Cl.
CPC .......... *A61B 5/7282* (2013.01); *A61B 5/0022* (2013.01); *A61B 5/02028* (2013.01);
(Continued)

(58) Field of Classification Search
CPC .............. A61B 5/0022; A61B 5/02028; A61B 5/02055; A61B 5/0295; A61B 5/145; A61B 5/6802; A61B 5/746
See application file for complete search history.

(56) References Cited

U.S. PATENT DOCUMENTS

| 4,246,344 A | 1/1981 | Silver, III | G01N 33/5094 |
| 5,025,791 A * | 6/1991 | Niwa | A61B 5/14552 600/324 |

(Continued)

OTHER PUBLICATIONS

U.S. Appl. No. 14/333,341, filed Jul. 16, 2014, Berz.
(Continued)

*Primary Examiner* — Christopher A Flory
(74) *Attorney, Agent, or Firm* — HAYES SOLOWAY P.C.

(57) ABSTRACT

Systems and methods for home monitoring and detection of febrile neutropenia in a patient are provided. The system includes a photoplethysmographic sensor for sensing photoplethysmographic signals of the patient, and one or more blood borne parameter sensors for sensing parameters in the patient's blood. A febrile neutropenia monitoring application receives information sensed by the photoplethysmography sensor and the one or more blood borne parameter sensors and determines, based on the received information, the presence or deterioration of febrile neutropenia. The method includes the steps of: sensing photoplethysmographic signals of the patient with a photoplethysmographic sensor worn by the patient; sensing blood borne parameters in the patient's blood with one or more blood borne parameter sensors; transmitting the sensed photoplethysmographic signals and blood borne parameters to a febrile neutropenia monitoring application; and determining, by the febrile neutropenia monitoring application, the presence or deterioration of febrile neutropenia based on the received information.

17 Claims, 3 Drawing Sheets

Related U.S. Application Data which is a continuation of application No. 14/333,341, filed on Jul. 16, 2014, now Pat. No. 10,314,549.

(60) Provisional application No. 61/846,980, filed on Jul. 16, 2013.

(51) Int. Cl.
*A61B 5/0205* (2006.01)
*A61B 5/0295* (2006.01)
*A61B 5/145* (2006.01)

(52) U.S. Cl.
CPC .......... *A61B 5/0295* (2013.01); *A61B 5/4833* (2013.01); *A61B 5/746* (2013.01); *A61B 5/02055* (2013.01); *A61B 5/145* (2013.01); *A61B 5/6802* (2013.01); *A61B 5/7207* (2013.01)

(56) References Cited

U.S. PATENT DOCUMENTS

| | | | | |
|---|---|---|---|---|
| 5,967,975 | A | 10/1999 | Ridgeway | G06F 19/3418 |
| 6,594,011 | B1 | 7/2003 | Kempen | 356/369 |
| 6,859,280 | B2 | 2/2005 | Kempen | 356/369 |
| 6,882,420 | B2 | 4/2005 | Rassman et al. | 356/369 |
| 7,002,686 | B2 | 2/2006 | Lieberman et al. | 356/369 |
| 7,023,547 | B2 | 4/2006 | Venkatasubbarao et al. | 356/369 |
| 7,193,711 | B2 | 3/2007 | Rassman et al. | 356/369 |
| 7,518,724 | B2 | 4/2009 | Rassman et al. | 356/369 |
| 7,890,153 | B2 | 2/2011 | Hoarau | A61B 5/062 |
| 8,039,270 | B2 | 10/2011 | Dultz et al. | 436/518 |
| 8,355,133 | B2 | 1/2013 | Dultz et al. | 356/445 |
| 2005/0209516 | A1* | 9/2005 | Fraden | A61B 5/14552 600/323 |
| 2006/0085227 | A1* | 4/2006 | Rosenfeld | G16H 80/00 600/301 |
| 2007/0043269 | A1 | 2/2007 | Mannheimer | A61B 5/14551 |
| 2007/0273504 | A1* | 11/2007 | Tran | A61B 5/14532 340/539.12 |

OTHER PUBLICATIONS

U.S. Appl. No. 16/436,035, filed Jun. 10, 2019, Berz.

Children's Hospital of Orange County ("Febrile Neutropenia Oncology Care Guideline" 2011.

Penack et al. "Management of sepsis in neutropenic patients: guidelines from the infectious diseases working party of the German Society of Hematology and Oncology" Annals of Oncology, vol. 22, Issue 5, May 1, 2011, pp. 1019-1029 (Published Nov. 1, 2010).

Povoa P, Souza-Dantas VC, Soares M, Salluh JF C-reactive protein in critically ill cancer patients with sepsis: influence of neutropenia Crit Care. 2011,15(3):R129. doi: 10.1186/cc10242. Epub May 19, 2011.

Sakr, Y., Sponholz, C., Tuche, F. et al. The Role of Procalcitonin in Febrile Neutropenic Patients: Review of the Literature. Infection (2008) 36: 396. doi:10.1007/s15010-008-7374-y.

Uzun, O, Anaissie E. Outpatient therapy for febrile neutropenia: who, when and how?. Antimicrob. Chemother. (1999)43 (3): 317-320.doi: 10.1093/jac/43.3.317.

* cited by examiner

100

102 — Meeting all 3 Criteria
- Recent chemotherapy exposure
- ANC less than or equal to 1,000/rnm3
- Temperature greater than or equal to 38.3°C

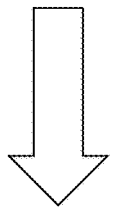

104 — Initial Assessment
1. Complete Physical Exam
2. CBC and CMP
3. Urinalysis
4. Lactic Acid
5. Microbiologic assessment-Urine culture and sensitivity, Blood Cultures (with a set collected from each lumen simultaneously if CVC present, and 1 peripheral. If no CVC present 2 blood cultures from separate venipuncture sites) and other cultures as clinically indicated
6. CXR if clinically indicated (signs/symptoms of respiratory involvement)
7. Perform risk assessment with MASCC score If meets low risk MSACC score 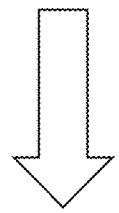

106
1. Solid tumor
2. Lives within 1 hour travel time of the treating center/physician
3. Able to tolerate oral medications and fluids
4. Does not use PEG as route for nutrition and
5. Not currently on antibiotics
6. 18 years old or over
7. No quinolone allergy for oral regimens

FIG. 1

METHOD AND APPARATUS FOR MONITORING DEVELOPMENT OF MEDICATION INDUCED SIDE EFFECTS

CROSS REFERENCE TO RELATED APPLICATIONS

This application is a continuation-in-part of my U.S. patent application Ser. No. 16/436,035, filed Jun. 10, 2019, which is turn is a continuation application of U.S. patent application Ser. No. 14/333,341, filed Jul. 16, 2014, now U.S. Pat. No. 10,314,549, granted Jun. 11, 2019, which in turn, claims priority from U.S. Provisional Application Ser. No. 61/846,980, filed Jul. 16, 2013, the contents of which are incorporated herein by reference.

FIELD OF THE INVENTION

The present disclosure is generally related to home monitoring of a patient's health, and more particularly is related to systems and methods home monitoring and detection of medication induced side effects in a patient.

BACKGROUND OF THE INVENTION

Various drugs and drug combinations currently are used in treating cancer. These drugs include
- 5-FU (Fluorouracil Injection) indicated for Breast Cancer
- 5-FU (Fluorouracil Injection) indicated for Colon Cancer
- 5-FU (Fluorouracil Injection) indicated for Gastric Cancer
- 5-FU (Fluorouracil Injection) indicated for Pancreatic Cancer
- 5-FU (Fluorouracil Injection) indicated for Rectal Cancer
- 5-FU (Fluorouracil—Topical) indicated for Basal Cell Carcinoma
- Abecma (Idecabtagene Vicleucel) indicated for Multiple Myeloma
- Abemaciclib indicated for Breast Cancer
- Abiraterone Acetate indicated for Prostate Cancer
- Abraxane (Paclitaxel Albumin-stabilized Nanoparticle Formulation) indicated for Breast Cancer
- Abraxane (Paclitaxel Albumin-stabilized Nanoparticle Formulation) indicated for Non-Small Cell Lung Cancer
- Abraxane (Paclitaxel Albumin-stabilized Nanoparticle Formulation) indicated for Pancreatic Cancer
- Acalabrutinib indicated for Chronic Lymphocytic Leukemia
- Acalabrutinib indicated for Non-Hodgkin Lymphoma
- Adcetris (Brentuximab Vedotin) indicated for Hodgkin Lymphoma
- Adcetris (Brentuximab Vedotin) indicated for Non-Hodgkin Lymphoma
- Ado-Trastuzumab Emtansine indicated for Breast Cancer
- Adriamycin PFS (Doxorubicin Hydrochloride) indicated for Myeloproliferative Neoplasms
- Adriamycin RDF (Doxorubicin Hydrochloride) indicated for Myeloproliferative Neoplasms
- Afatinib Dimaleate indicated for Non-Small Cell Lung Cancer
- Afinitor (Everolimus) indicated for Brain Tumors
- Afinitor (Everolimus) indicated for Breast Cancer
- Afinitor (Everolimus) indicated for Gastroenteropancreatic Neuroendocrine Tumors
- Afinitor (Everolimus) indicated for Non-Small Cell Lung Cancer
- Afinitor (Everolimus) indicated for Pancreatic Cancer
- Afinitor (Everolimus) indicated for Renal Cell Cancer
- Afinitor (Everolimus) indicated for Small Cell Lung Cancer
- Afinitor Disperz (Everolimus) indicated for Brain Tumors
- Afinitor Disperz (Everolimus) indicated for Breast Cancer
- Afinitor Disperz (Everolimus) indicated for Gastroenteropancreatic Neuroendocrine Tumors
- Afinitor Disperz (Everolimus) indicated for Non-Small Cell Lung Cancer
- Afinitor Disperz (Everolimus) indicated for Renal Cell Cancer
- Aldara (Imiquimod) indicated for Basal Cell Carcinoma
- Aldesleukin indicated for Melanoma
- Aldesleukin indicated for Melanoma
- Aldesleukin indicated for Renal Cell Cancer
- Alecensa (Alectinib) indicated for Non-Small Cell Lung Cancer
- Alectinib indicated for Non-Small Cell Lung Cancer
- Alemtuzumab indicated for Chronic Lymphocytic Leukemia
- Alimta (Pemetrexed Disodium) indicated for Malignant Mesothelioma
- Alimta (Pemetrexed Disodium) indicated for Non-Small Cell Lung Cancer
- Aliqopa (Copanlisib Hydrochloride) indicated for Non-Hodgkin Lymphoma
- Alkeran (Melphalan) indicated for Ovarian Cancer
- Alkeran for Injection (Melphalan Hydrochloride) indicated for Multiple Myeloma
- Alkeran Tablets (Melphalan) indicated for Multiple Myeloma
- Alpelisib indicated for Breast Cancer
- Alunbrig (Brigatinib) indicated for Non-Small Cell Lung Cancer
- Anastrozole indicated for Breast Cancer
- Apalutamide indicated for Prostate Cancer
- Aredia (Pamidronate Disodium) indicated for Breast Cancer
- Aredia (Pamidronate Disodium) indicated for Multiple Myeloma
- Arimidex (Anastrozole) indicated for Breast Cancer
- Aromasin (Exemestane) indicated for Breast Cancer
- Arranon (Nelarabine) indicated for Acute Lymphoblastic Leukemia
- Arranon (Nelarabine) indicated for Non-Hodgkin Lymphoma
- Arsenic Trioxide indicated for Acute Myeloid Leukemia
- Arsenic Trioxide indicated for Myeloproliferative Neoplasms
- Arzerra (Ofatumumab) indicated for Chronic Lymphocytic Leukemia
- Asparaginase *Erwinia chrysanthemi* indicated for Acute Lymphoblastic Leukemia
- Asparlas (Calaspargase Pegol-mknl) indicated for Acute Lymphoblastic Leukemia
- Atezolizumab indicated for Bladder Cancer
- Atezolizumab indicated for Breast Cancer
- Atezolizumab indicated for Liver Cancer
- Atezolizumab indicated for Non-Small Cell Lung Cancer
- Atezolizumab indicated for Small Cell Lung Cancer
- Avapritinib indicated for Gastrointestinal Stromal Tumors
- Avastin (Bevacizumab) indicated for Brain Tumors
- Avastin (Bevacizumab) indicated for Cervical Cancer
- Avastin (Bevacizumab) indicated for Colon Cancer
- Avastin (Bevacizumab) indicated for Liver Cancer Avastin (Bevacizumab) indicated for Non-Small Cell Lung Cancer
Avastin (Bevacizumab) indicated for Ovarian Cancer
Avastin (Bevacizumab) indicated for Rectal Cancer
Avastin (Bevacizumab) indicated for Renal Cell Cancer
Avelumab indicated for Bladder Cancer
Avelumab indicated for Merkel Cell Carcinoma
Avelumab indicated for Renal Cell Cancer
Axicabtagene Ciloleucel indicated for Non-Hodgkin Lymphoma
Axitinib indicated for Renal Cell Cancer
Ayvakit (Avapritinib) indicated for Gastrointestinal Stromal Tumors
Azacitidine indicated for Acute Myeloid Leukemia
Azacitidine indicated for Myeloproliferative Neoplasms
Azedra (Iobenguane I 131) indicated for Paraganglioma
Azedra (Iobenguane I 131) indicated for Pheochromocytoma
Balversa (Erdafitinib) indicated for Bladder Cancer
Bavencio (Avelumab) indicated for Bladder Cancer
Bavencio (Avelumab) indicated for Merkel Cell Carcinoma
Bavencio (Avelumab) indicated for Renal Cell Cancer
Belantamab Mafodotin-blmf indicated for Multiple Myeloma
Beleodaq (Belinostat) indicated for Non-Hodgkin Lymphoma
Belinostat indicated for Non-Hodgkin Lymphoma
Bendamustine Hydrochloride indicated for Chronic Lymphocytic Leukemia
Bendamustine Hydrochloride indicated for Non-Hodgkin Lymphoma
Bendeka (Bendamustine Hydrochloride) indicated for Chronic Lymphocytic Leukemia
Bendeka (Bendamustine Hydrochloride) indicated for Non-Hodgkin Lymphoma
Besponsa (Inotuzumab Ozogamicin) indicated for Acute Lymphoblastic Leukemia
Bevacizumab indicated for Brain Tumors
Bevacizumab indicated for Cervical Cancer
Bevacizumab indicated for Colon Cancer
Bevacizumab indicated for Liver Cancer
Bevacizumab indicated for Non-Small Cell Lung Cancer
Bevacizumab indicated for Ovarian Cancer
Bevacizumab indicated for Rectal Cancer
Bevacizumab indicated for Renal Cell Cancer
Bicalutamide indicated for Prostate Cancer
BiCNU (Carmustine) indicated for Brain Tumors
BiCNU (Carmustine) indicated for Hodgkin Lymphoma
BiCNU (Carmustine) indicated for Multiple Myeloma
BiCNU (Carmustine) indicated for Non-Hodgkin Lymphoma
Binimetinib indicated for Melanoma
Blenrep (Belantamab Mafodotin-blmf) indicated for Multiple Myeloma
Bleomycin Sulfate indicated for Cervical Cancer
Bleomycin Sulfate indicated for Head and Neck Cancer
Bleomycin Sulfate indicated for Hodgkin Lymphoma
Bleomycin Sulfate indicated for Non-Hodgkin Lymphoma
Bleomycin Sulfate indicated for Penile Cancer
Bleomycin Sulfate indicated for Testicular Cancer
Bleomycin Sulfate indicated for Vulvar Cancer
Blinatumomab indicated for Acute Lymphoblastic Leukemia
Blincyto (Blinatumomab) indicated for Acute Lymphoblastic Leukemia
Bortezomib indicated for Multiple Myeloma
Bortezomib indicated for Non-Hodgkin Lymphoma
Bosulif (Bosutinib) indicated for Chronic Myelogenous Leukemia
Bosutinib indicated for Chronic Myelogenous Leukemia
Braftovi (Encorafenib) indicated for Melanoma
Brentuximab Vedotin indicated for Hodgkin Lymphoma
Brentuximab Vedotin indicated for Non-Hodgkin Lymphoma
Brexucabtagene Autoleucel indicated for Non-Hodgkin Lymphoma
Breyanzi (Lisocabtagene Maraleucel) indicated for Non-Hodgkin Lymphoma
Brigatinib indicated for Non-Small Cell Lung Cancer
Brukinsa (Zanubrutinib) indicated for Non-Hodgkin Lymphoma
Busulfan indicated for Chronic Myelogenous Leukemia
Busulfex (Busulfan) indicated for Chronic Myelogenous Leukemia
Cabazitaxel indicated for Prostate Cancer
Cabometyx (Cabozantinib-S-Malate) indicated for Liver Cancer
Cabometyx (Cabozantinib-S-Malate) indicated for Renal Cell Cancer
Cabozantinib-S-Malate indicated for Liver Cancer
Cabozantinib-S-Malate indicated for Renal Cell Cancer
Cabozantinib-S-Malate indicated for Thyroid Cancer
Calaspargase Pegol-mknl indicated for Acute Lymphoblastic Leukemia
Calquence (Acalabrutinib) indicated for Chronic Lymphocytic Leukemia
Calquence (Acalabrutinib) indicated for Non-Hodgkin Lymphoma
Campath (Alemtuzumab) indicated for Chronic Lymphocytic Leukemia
Camptosar (Irinotecan Hydrochloride) indicated for Colon Cancer
Camptosar (Irinotecan Hydrochloride) indicated for Rectal Cancer
Capecitabine indicated for Breast Cancer
Capecitabine indicated for Colon Cancer
Capecitabine indicated for Rectal Cancer
Capmatinib Hydrochloride indicated for Non-Small Cell Lung Cancer
Caprelsa (Vandetanib) indicated for Thyroid Cancer
Carboplatin indicated for Non-Small Cell Lung Cancer
Carboplatin indicated for Ovarian Cancer
Carfilzomib indicated for Multiple Myeloma
Carmustine Implant indicated for Brain Tumors
Carmustine indicated for Brain Tumors
Carmustine indicated for Hodgkin Lymphoma
Carmustine indicated for Multiple Myeloma
Carmustine indicated for Non-Hodgkin Lymphoma
Casodex (Bicalutamide) indicated for Prostate Cancer
Cemiplimab-rwlc indicated for Basal Cell Carcinoma
Cemiplimab-rwlc indicated for Cutaneous Squamous Cell Carcinoma
Cemiplimab-rwlc indicated for Non-Small Cell Lung Cancer
Ceritinib indicated for Non-Small Cell Lung Cancer
Cerubidine (Daunorubicin Hydrochloride) indicated for Acute Lymphoblastic Leukemia
Cerubidine (Daunorubicin Hydrochloride) indicated for Acute Myeloid Leukemia
Cerubidine (Daunorubicin Hydrochloride) indicated for Myeloproliferative Neoplasms
Cetuximab indicated for Colon Cancer Cetuximab indicated for Head and Neck Cancer
Cetuximab indicated for Rectal Cancer
Chlorambucil indicated for Chronic Lymphocytic Leukemia
Chlorambucil indicated for Hodgkin Lymphoma
Chlorambucil indicated for Non-Hodgkin Lymphoma
Cisplatin indicated for Bladder Cancer
Cisplatin indicated for Ovarian Cancer
Cisplatin indicated for Testicular Cancer
Cladribine indicated for Hairy Cell Leukemia
Clafen (Cyclophosphamide) indicated for Myeloproliferative Neoplasms
Clofarabine indicated for Acute Lymphoblastic Leukemia
Clolar (Clofarabine) indicated for Acute Lymphoblastic Leukemia
Cobimetinib Fumarate indicated for Melanoma
Cobimetinib indicated for Melanoma
Cometriq (Cabozantinib-S-Malate) indicated for Thyroid Cancer
Copanlisib Hydrochloride indicated for Non-Hodgkin Lymphoma
Copiktra (Duvelisib) indicated for Chronic Lymphocytic Leukemia
Copiktra (Duvelisib) indicated for Non-Hodgkin Lymphoma
Cosmegen (Dactinomycin) indicated for Bone Cancer
Cosmegen (Dactinomycin) indicated for Childhood Kidney Cancers
Cosmegen (Dactinomycin) indicated for Gestational Trophoblastic Disease
Cosmegen (Dactinomycin) indicated for Rhabdomyosarcoma
Cosmegen (Dactinomycin) indicated for Soft Tissue Sarcoma
Cosmegen (Dactinomycin) indicated for Testicular Cancer
Cotellic (Cobimetinib Fumarate) indicated for Melanoma
Cotellic (Cobimetinib) indicated for Melanoma
Crizotinib indicated for Non-Hodgkin Lymphoma
Crizotinib indicated for Non-Small Cell Lung Cancer
Cyclophosphamide indicated for Acute Lymphoblastic Leukemia
Cyclophosphamide indicated for Acute Myeloid Leukemia
Cyclophosphamide indicated for Breast Cancer
Cyclophosphamide indicated for Chronic Lymphocytic Leukemia
Cyclophosphamide indicated for Chronic Myelogenous Leukemia
Cyclophosphamide indicated for Hodgkin Lymphoma
Cyclophosphamide indicated for Multiple Myeloma
Cyclophosphamide indicated for Myeloproliferative Neoplasms
Cyclophosphamide indicated for Neuroblastoma
Cyclophosphamide indicated for Non-Hodgkin Lymphoma
Cyclophosphamide indicated for Ovarian Cancer
Cyclophosphamide indicated for Retinoblastoma
Cyramza (Ramucirumab) indicated for Colon Cancer
Cyramza (Ramucirumab) indicated for Gastric Cancer
Cyramza (Ramucirumab) indicated for Gastroesophageal Junction Cancer
Cyramza (Ramucirumab) indicated for Liver Cancer
Cyramza (Ramucirumab) indicated for Non-Small Cell Lung Cancer
Cyramza (Ramucirumab) indicated for Rectal Cancer
Cytarabine indicated for Acute Lymphoblastic Leukemia
Cytarabine indicated for Acute Myeloid Leukemia
Cytarabine indicated for Chronic Myelogenous Leukemia
Cytarabine indicated for Meningeal Leukemia
Cytarabine indicated for Myeloproliferative Neoplasms
Cytosar-U (Cytarabine) indicated for Myeloproliferative Neoplasms
Cytoxan (Cyclophosphamide) indicated for Myeloproliferative Neoplasms
Dabrafenib indicated for Melanoma
Dabrafenib Mesylate indicated for Melanoma
Dabrafenib Mesylate indicated for Non-Small Cell Lung Cancer
Dabrafenib Mesylate indicated for Thyroid Cancer
Dacarbazine indicated for Hodgkin Lymphoma
Dacarbazine indicated for Melanoma
Dacarbazine indicated for Melanoma
Dacogen (Decitabine) indicated for Myeloproliferative Neoplasms
Dacomitinib indicated for Non-Small Cell Lung Cancer
Dactinomycin indicated for Bone Cancer
Dactinomycin indicated for Childhood Kidney Cancers
Dactinomycin indicated for Gestational Trophoblastic Disease
Dactinomycin indicated for Rhabdomyosarcoma
Dactinomycin indicated for Soft Tissue Sarcoma
Dactinomycin indicated for Testicular Cancer
Danyelza (Naxitamab-gqgk) indicated for Brain Tumors
Danyelza (Naxitamab-gqgk) indicated for Neuroblastoma
Daratumumab and Hyaluronidase-fihj indicated for Multiple Myeloma
Daratumumab indicated for Multiple Myeloma
Darolutamide indicated for Prostate Cancer
Darzalex (Daratumumab) indicated for Multiple Myeloma
Darzalex Faspro (Daratumumab and Hyaluronidase-fihj) indicated for Multiple Myeloma
Dasatinib indicated for Acute Lymphoblastic Leukemia
Dasatinib indicated for Chronic Myelogenous Leukemia
Dasatinib indicated for Myeloproliferative Neoplasms
Daunorubicin Hydrochloride and Cytarabine Liposome indicated for Acute Myeloid Leukemia
Daunorubicin Hydrochloride indicated for Acute Lymphoblastic Leukemia
Daunorubicin Hydrochloride indicated for Acute Myeloid Leukemia
Daunorubicin Hydrochloride indicated for Myeloproliferative Neoplasms
Daurismo (Glasdegib Maleate) indicated for Acute Myeloid Leukemia
Decitabine and Cedazuridine indicated for Myeloproliferative Neoplasms
Decitabine indicated for Myeloproliferative Neoplasms
Degarelix indicated for Prostate Cancer
Denileukin Diftitox indicated for Non-Hodgkin Lymphoma
Denosumab indicated for Bone Cancer
Dexamethasone indicated for Acute Lymphoblastic Leukemia
Dexamethasone indicated for Acute Myeloid Leukemia
Dexamethasone indicated for Chronic Lymphocytic Leukemia
Dexamethasone indicated for Chronic Myelogenous Leukemia
Dexamethasone indicated for Hodgkin Lymphoma
Dexamethasone indicated for Non-Hodgkin Lymphoma
Dinutuximab indicated for Neuroblastoma
Docetaxel indicated for Breast Cancer Docetaxel indicated for Gastric Cancer
Docetaxel indicated for Gastroesophageal Junction Cancer
Docetaxel indicated for Head and Neck Cancer
Docetaxel indicated for Non-Small Cell Lung Cancer
Docetaxel indicated for Prostate Cancer
Dostarlimab-gxly indicated for Endometrial Cancer
Doxil (Doxorubicin Hydrochloride Liposome) indicated for Kaposi Sarcoma
Doxil (Doxorubicin Hydrochloride Liposome) indicated for Multiple Myeloma
Doxil (Doxorubicin Hydrochloride Liposome) indicated for Ovarian Cancer
Doxorubicin Hydrochloride indicated for Acute Lymphoblastic Leukemia
Doxorubicin Hydrochloride indicated for Acute Myeloid Leukemia
Doxorubicin Hydrochloride indicated for Bladder Cancer
Doxorubicin Hydrochloride indicated for Bone Cancer
Doxorubicin Hydrochloride indicated for Breast Cancer
Doxorubicin Hydrochloride indicated for Childhood Kidney Cancers
Doxorubicin Hydrochloride indicated for Gastric Cancer
Doxorubicin Hydrochloride indicated for Hodgkin Lymphoma
Doxorubicin Hydrochloride indicated for Myeloproliferative Neoplasms
Doxorubicin Hydrochloride indicated for Neuroblastoma
Doxorubicin Hydrochloride indicated for Non-Hodgkin Lymphoma
Doxorubicin Hydrochloride indicated for Non-Small Cell Lung Cancer
Doxorubicin Hydrochloride indicated for Ovarian Cancer
Doxorubicin Hydrochloride indicated for Small Cell Lung Cancer
Doxorubicin Hydrochloride indicated for Soft Tissue Sarcoma
Doxorubicin Hydrochloride indicated for Thyroid Cancer
Doxorubicin Hydrochloride Liposome indicated for Kaposi Sarcoma
Doxorubicin Hydrochloride Liposome indicated for Multiple Myeloma
Doxorubicin Hydrochloride Liposome indicated for Ovarian Cancer
DTIC-Dome (Dacarbazine) indicated for Melanoma
Durvalumab indicated for Non-Small Cell Lung Cancer
Durvalumab indicated for Small Cell Lung Cancer
Duvelisib indicated for Chronic Lymphocytic Leukemia
Duvelisib indicated for Non-Hodgkin Lymphoma
Efudex (Fluorouracil—Topical) indicated for Basal Cell Carcinoma
Eligard (Leuprolide Acetate) indicated for Prostate Cancer
Ellence (Epirubicin Hydrochloride) indicated for Breast Cancer
Elotuzumab indicated for Multiple Myeloma
Eloxatin (Oxaliplatin) indicated for Colon Cancer
Eloxatin (Oxaliplatin) indicated for Rectal Cancer
Elzonris (Tagraxofusp-erzs) indicated for Blastic Plasmacytoid Dendritic Cell Neoplasm
Empliciti (Elotuzumab) indicated for Multiple Myeloma
Enasidenib Mesylate indicated for Acute Myeloid Leukemia
Encorafenib indicated for Melanoma
Enfortumab Vedotin-ejfv indicated for Bladder Cancer
Enhertu (Fam-Trastuzumab Deruxtecan-nxki) indicated for Breast Cancer
Enhertu (Fam-Trastuzumab Deruxtecan-nxki) indicated for Gastric Cancer
Enhertu (Fam-Trastuzumab Deruxtecan-nxki) indicated for Gastroesophageal Junction Cancer
Entrectinib indicated for All Solid Tumors
Entrectinib indicated for Non-Small Cell Lung Cancer
Enzalutamide indicated for Prostate Cancer
Epirubicin Hydrochloride indicated for Breast Cancer
Erbitux (Cetuximab) indicated for Colon Cancer
Erbitux (Cetuximab) indicated for Head and Neck Cancer
Erbitux (Cetuximab) indicated for Rectal Cancer
Erdafitinib indicated for Bladder Cancer
Eribulin Mesylate indicated for Breast Cancer
Eribulin Mesylate indicated for Soft Tissue Sarcoma
Erivedge (Vismodegib) indicated for Basal Cell Carcinoma
Erleada (Apalutamide) indicated for Prostate Cancer
Erlotinib Hydrochloride indicated for Non-Small Cell Lung Cancer
Erlotinib Hydrochloride indicated for Pancreatic Cancer
Erwinaze (Asparaginase *Erwinia Chrysanthemi*) indicated for Acute Lymphoblastic Leukemia
Etopophos (Etoposide Phosphate) indicated for Small Cell Lung Cancer
Etopophos (Etoposide Phosphate) indicated for Testicular Cancer
Etoposide indicated for Small Cell Lung Cancer
Etoposide indicated for Testicular Cancer
Etoposide Phosphate indicated for Small Cell Lung Cancer
Etoposide Phosphate indicated for Testicular Cancer
Everolimus indicated for Brain Tumors
Everolimus indicated for Breast Cancer
Everolimus indicated for Gastroenteropancreatic Neuroendocrine Tumors
Everolimus indicated for Non-Small Cell Lung Cancer
Everolimus indicated for Pancreatic Cancer
Everolimus indicated for Renal Cell Cancer
Everolimus indicated for Small Cell Lung Cancer
Evomela (Melphalan Hydrochloride) indicated for Multiple Myeloma
Exemestane indicated for Breast Cancer
Fam-Trastuzumab Deruxtecan-nxki indicated for Breast Cancer
Fam-Trastuzumab Deruxtecan-nxki indicated for Gastric Cancer
Fam-Trastuzumab Deruxtecan-nxki indicated for Gastroesophageal Junction Cancer
Fareston (Toremifene) indicated for Breast Cancer
Farydak (Panobinostat Lactate) indicated for Multiple Myeloma
Faslodex (Fulvestrant) indicated for Breast Cancer
Fedratinib Hydrochloride indicated for Myeloproliferative Neoplasms
Femara (Letrozole) indicated for Breast Cancer
Firmagon (Degarelix) indicated for Prostate Cancer
Fludarabine Phosphate indicated for Chronic Lymphocytic Leukemia
Fluorouracil Injection indicated for Breast Cancer
Fluorouracil Injection indicated for Colon Cancer
Fluorouracil Injection indicated for Gastric Cancer
Fluorouracil Injection indicated for Pancreatic Cancer
Fluorouracil Injection indicated for Rectal Cancer
Fluorouracil—Topical indicated for Basal Cell Carcinoma
Flutamide indicated for Prostate Cancer Folotyn (Pralatrexate) indicated for Non-Hodgkin Lymphoma
Fotivda (Tivozanib Hydrochloride) indicated for Renal Cell Cancer
Fulvestrant indicated for Breast Cancer
Gavreto (Pralsetinib) indicated for Non-Small Cell Lung Cancer
Gavreto (Pralsetinib) indicated for Thyroid Cancer
Gazyva (Obinutuzumab) indicated for Chronic Lymphocytic Leukemia
Gazyva (Obinutuzumab) indicated for Non-Hodgkin Lymphoma
Gefitinib indicated for Non-Small Cell Lung Cancer
Gemcitabine Hydrochloride indicated for Breast Cancer
Gemcitabine Hydrochloride indicated for Non-Small Cell Lung Cancer
Gemcitabine Hydrochloride indicated for Ovarian Cancer
Gemcitabine Hydrochloride indicated for Pancreatic Cancer
Gemtuzumab Ozogamicin indicated for Acute Myeloid Leukemia
Gemzar (Gemcitabine Hydrochloride) indicated for Breast Cancer
Gemzar (Gemcitabine Hydrochloride) indicated for Non-Small Cell Lung Cancer
Gemzar (Gemcitabine Hydrochloride) indicated for Ovarian Cancer
Gemzar (Gemcitabine Hydrochloride) indicated for Pancreatic Cancer
Gilotrif (Afatinib Dimaleate) indicated for Non-Small Cell Lung Cancer
Gilteritinib Fumarate indicated for Acute Myeloid Leukemia
Glasdegib Maleate indicated for Acute Myeloid Leukemia
Gleevec (Imatinib Mesylate) indicated for Acute Lymphoblastic Leukemia
Gleevec (Imatinib Mesylate) indicated for Chronic Myelogenous Leukemia
Gleevec (Imatinib Mesylate) indicated for Gastrointestinal Stromal Tumors
Gleevec (Imatinib Mesylate) indicated for Myeloproliferative Neoplasms
Gleevec (Imatinib Mesylate) indicated for Soft Tissue Sarcoma
Gliadel Wafer (Carmustine Implant) indicated for Brain Tumors
Goserelin Acetate indicated for Breast Cancer
Goserelin Acetate indicated for Prostate Cancer
Halaven (Eribulin Mesylate) indicated for Breast Cancer
Halaven (Eribulin Mesylate) indicated for Soft Tissue Sarcoma
Hemangeol (Propranolol Hydrochloride) indicated for Pheochromocytoma
Herceptin (Trastuzumab) indicated for Breast Cancer
Herceptin (Trastuzumab) indicated for Gastric Cancer
Herceptin (Trastuzumab) indicated for Gastroesophageal Junction Cancer
Herceptin Hylecta (Trastuzumab and Hyaluronidase-oysk) indicated for Breast Cancer
Hycamtin (Topotecan Hydrochloride) indicated for Cervical Cancer
Hycamtin (Topotecan Hydrochloride) indicated for Ovarian Cancer
Hycamtin (Topotecan Hydrochloride) indicated for Small Cell Lung Cancer
Hydrea (Hydroxyurea) indicated for Chronic Myelogenous Leukemia
Hydrea (Hydroxyurea) indicated for Head and Neck Cancer
Hydroxyurea indicated for Chronic Myelogenous Leukemia
Hydroxyurea indicated for Head and Neck Cancer
Ibrance (Palbociclib) indicated for Breast Cancer
Ibritumomab Tiuxetan indicated for Non-Hodgkin Lymphoma
Ibrutinib indicated for Chronic Lymphocytic Leukemia
Ibrutinib indicated for Non-Hodgkin Lymphoma
Iclusig (Ponatinib Hydrochloride) indicated for Acute Lymphoblastic Leukemia
Iclusig (Ponatinib Hydrochloride) indicated for Chronic Myelogenous Leukemia
Idamycin PFS (Idarubicin Hydrochloride) indicated for Acute Myeloid Leukemia
Idarubicin Hydrochloride indicated for Acute Myeloid Leukemia
Idecabtagene Vicleucel indicated for Multiple Myeloma
Idelalisib indicated for Chronic Lymphocytic Leukemia
Idelalisib indicated for Non-Hodgkin Lymphoma
Idhifa (Enasidenib Mesylate) indicated for Acute Myeloid Leukemia
Ifex (Ifosfamide) indicated for Testicular Cancer
Ifosfamide indicated for Testicular Cancer
IL-2 (Aldesleukin) indicated for Melanoma
IL-2 (Aldesleukin) indicated for Melanoma
IL-2 (Aldesleukin) indicated for Renal Cell Cancer
Imatinib Mesylate indicated for Acute Lymphoblastic Leukemia
Imatinib Mesylate indicated for Chronic Myelogenous Leukemia
Imatinib Mesylate indicated for Gastrointestinal Stromal Tumors
Imatinib Mesylate indicated for Myeloproliferative Neoplasms
Imatinib Mesylate indicated for Soft Tissue Sarcoma
Imbruvica (Ibrutinib) indicated for Chronic Lymphocytic Leukemia
Imbruvica (Ibrutinib) indicated for Non-Hodgkin Lymphoma
Imfinzi (Durvalumab) indicated for Non-Small Cell Lung Cancer
Imfinzi (Durvalumab) indicated for Small Cell Lung Cancer
Imiquimod indicated for Basal Cell Carcinoma
Imlygic (Talimogene Laherparepvec) indicated for Melanoma
Imlygic (Talimogene Laherparepvec) indicated for Melanoma
Infugem (Gemcitabine Hydrochloride) indicated for Breast Cancer
Infugem (Gemcitabine Hydrochloride) indicated for Non-Small Cell Lung Cancer
Infugem (Gemcitabine Hydrochloride) indicated for Ovarian Cancer
Infugem (Gemcitabine Hydrochloride) indicated for Pancreatic Cancer
Inlyta (Axitinib) indicated for Renal Cell Cancer
Inotuzumab Ozogamicin indicated for Acute Lymphoblastic Leukemia
Inqovi (Decitabine and Cedazuridine) indicated for Myeloproliferative Neoplasms
Inrebic (Fedratinib Hydrochloride) indicated for Myeloproliferative Neoplasms Interleukin-2 (Aldesleukin) indicated for Melanoma
Interleukin-2 (Aldesleukin) indicated for Melanoma
Interleukin-2 (Aldesleukin) indicated for Renal Cell Cancer
Intron A (Recombinant Interferon Alfa-2b) indicated for Hairy Cell Leukemia
Intron A (Recombinant Interferon Alfa-2b) indicated for Kaposi Sarcoma
Intron A (Recombinant Interferon Alfa-2b) indicated for Melanoma
Intron A (Recombinant Interferon Alfa-2b) indicated for Melanoma
Intron A (Recombinant Interferon Alfa-2b) indicated for Non-Hodgkin Lymphoma
Iobenguane I 131 indicated for Paraganglioma
Iobenguane I 131 indicated for Pheochromocytoma
Ipilimumab indicated for Colon Cancer
Ipilimumab indicated for Malignant Mesothelioma
Ipilimumab indicated for Melanoma
Ipilimumab indicated for Melanoma
Ipilimumab indicated for Non-Small Cell Lung Cancer
Ipilimumab indicated for Rectal Cancer
Ipilimumab indicated for Renal Cell Cancer
Iressa (Gefitinib) indicated for Non-Small Cell Lung Cancer
Irinotecan Hydrochloride indicated for Colon Cancer
Irinotecan Hydrochloride indicated for Rectal Cancer
Irinotecan Hydrochloride Liposome indicated for Pancreatic Cancer
Isatuximab-irfc indicated for Multiple Myeloma
Istodax (Romidepsin) indicated for Non-Hodgkin Lymphoma
Ivosidenib indicated for Acute Myeloid Leukemia
Ixabepilone indicated for Breast Cancer
Ixazomib Citrate indicated for Multiple Myeloma
Ixempra (Ixabepilone) indicated for Breast Cancer
Jakafi (Ruxolitinib Phosphate) indicated for Myeloproliferative Neoplasms
Jelmyto (Mitomycin) indicated for Bladder Cancer
Jelmyto (Mitomycin) indicated for Urothelial Cancer
Jemperli (Dostarlimab-gxly) indicated for Endometrial Cancer
Jevtana (Cabazitaxel) indicated for Prostate Cancer
Kadcyla (Ado-Trastuzumab Emtansine) indicated for Breast Cancer
Keytruda (Pembrolizumab) indicated for All Solid Tumors
Keytruda (Pembrolizumab) indicated for Bladder Cancer
Keytruda (Pembrolizumab) indicated for Breast Cancer
Keytruda (Pembrolizumab) indicated for Cervical Cancer
Keytruda (Pembrolizumab) indicated for Colon Cancer
Keytruda (Pembrolizumab) indicated for Cutaneous Squamous Cell Carcinoma
Keytruda (Pembrolizumab) indicated for Endometrial Cancer
Keytruda (Pembrolizumab) indicated for Esophageal Cancer
Keytruda (Pembrolizumab) indicated for Gastric Cancer
Keytruda (Pembrolizumab) indicated for Gastroesophageal Junction Cancer
Keytruda (Pembrolizumab) indicated for Head and Neck Cancer
Keytruda (Pembrolizumab) indicated for Hodgkin Lymphoma
Keytruda (Pembrolizumab) indicated for Liver Cancer
Keytruda (Pembrolizumab) indicated for Melanoma
Keytruda (Pembrolizumab) indicated for Melanoma
Keytruda (Pembrolizumab) indicated for Merkel Cell Carcinoma
Keytruda (Pembrolizumab) indicated for Non-Hodgkin Lymphoma
Keytruda (Pembrolizumab) indicated for Non-Small Cell Lung Cancer
Keytruda (Pembrolizumab) indicated for Rectal Cancer
Keytruda (Pembrolizumab) indicated for Renal Cell Cancer
Kisqali (Ribociclib) indicated for Breast Cancer
Kymriah (Tisagenlecleucel) indicated for Acute Lymphoblastic Leukemia
Kymriah (Tisagenlecleucel) indicated for Non-Hodgkin Lymphoma
Kyprolis (Carfilzomib) indicated for Multiple Myeloma
Lanreotide Acetate indicated for Gastroenteropancreatic Neuroendocrine Tumors
Lapatinib Ditosylate indicated for Breast Cancer
Larotrectinib Sulfate indicated for All Solid Tumors
Lenalidomide indicated for Multiple Myeloma
Lenalidomide indicated for Non-Hodgkin Lymphoma
Lenvatinib Mesylate indicated for Endometrial Cancer
Lenvatinib Mesylate indicated for Liver Cancer
Lenvatinib Mesylate indicated for Renal Cell Cancer
Lenvatinib Mesylate indicated for Thyroid Cancer
Lenvima (Lenvatinib Mesylate) indicated for Endometrial Cancer
Lenvima (Lenvatinib Mesylate) indicated for Liver Cancer
Lenvima (Lenvatinib Mesylate) indicated for Renal Cell Cancer
Lenvima (Lenvatinib Mesylate) indicated for Thyroid Cancer
Letrozole indicated for Breast Cancer
Leucovorin Calcium indicated for Colon Cancer
Leucovorin Calcium indicated for Rectal Cancer
Leukeran (Chlorambucil) indicated for Chronic Lymphocytic Leukemia
Leukeran (Chlorambucil) indicated for Hodgkin Lymphoma
Leukeran (Chlorambucil) indicated for Non-Hodgkin Lymphoma
Leuprolide Acetate indicated for Prostate Cancer
Libtayo (Cemiplimab-rwlc) indicated for Basal Cell Carcinoma
Libtayo (Cemiplimab-rwlc) indicated for Cutaneous Squamous Cell Carcinoma
Libtayo (Cemiplimab-rwlc) indicated for Non-Small Cell Lung Cancer
Lisocabtagene Maraleucel indicated for Non-Hodgkin Lymphoma
Lomustine indicated for Brain Tumors
Lomustine indicated for Hodgkin Lymphoma
Loncastuximab Tesirine-lpyl indicated for Non-Hodgkin Lymphoma
Lonsurf (Trifluridine and Tipiracil Hydrochloride) indicated for Colon Cancer
Lonsurf (Trifluridine and Tipiracil Hydrochloride) indicated for Gastric Cancer
Lonsurf (Trifluridine and Tipiracil Hydrochloride) indicated for Gastroesophageal Junction Cancer
Lonsurf (Trifluridine and Tipiracil Hydrochloride) indicated for Rectal Cancer
Lorbrena (Lorlatinib) indicated for Non-Small Cell Lung Cancer
Lorlatinib indicated for Non-Small Cell Lung Cancer Lumoxiti (Moxetumomab Pasudotox-tdfk) indicated for Hairy Cell Leukemia
Lupron Depot (Leuprolide Acetate) indicated for Prostate Cancer
Lurbinectedin indicated for Small Cell Lung Cancer
Lynparza (Olaparib) indicated for Breast Cancer
Lynparza (Olaparib) indicated for Ovarian Cancer
Lynparza (Olaparib) indicated for Pancreatic Cancer
Lynparza (Olaparib) indicated for Prostate Cancer
Margenza (Margetuximab-cmkb) indicated for Breast Cancer
Margetuximab-cmkb indicated for Breast Cancer
Marqibo (Vincristine Sulfate Liposome) indicated for Acute Lymphoblastic Leukemia
Matulane (Procarbazine Hydrochloride) indicated for Hodgkin Lymphoma
Megestrol Acetate indicated for Breast Cancer
Megestrol Acetate indicated for Endometrial Cancer
Mekinist (Trametinib Dimethyl Sulfoxide) indicated for Melanoma
Mekinist (Trametinib Dimethyl Sulfoxide) indicated for Melanoma
Mekinist (Trametinib Dimethyl Sulfoxide) indicated for Non-Small Cell Lung Cancer
Mekinist (Trametinib Dimethyl Sulfoxide) indicated for Thyroid Cancer
Mektovi (Binimetinib) indicated for Melanoma
Melphalan Flufenamide Hydrochloride indicated for Multiple Myeloma
Melphalan Hydrochloride indicated for Multiple Myeloma
Melphalan indicated for Multiple Myeloma
Melphalan indicated for Ovarian Cancer
Mercaptopurine indicated for Acute Lymphoblastic Leukemia
Methotrexate Sodium indicated for Acute Lymphoblastic Leukemia
Methotrexate Sodium indicated for Bone Cancer
Methotrexate Sodium indicated for Breast Cancer
Methotrexate Sodium indicated for Gestational Trophoblastic Disease
Methotrexate Sodium indicated for Head and Neck Cancer
Methotrexate Sodium indicated for Non-Hodgkin Lymphoma
Methotrexate Sodium indicated for Non-Small Cell Lung Cancer
Methotrexate Sodium indicated for Small Cell Lung Cancer
Midostaurin indicated for Acute Myeloid Leukemia
Midostaurin indicated for Mast Cell Leukemia
Mitomycin indicated for Bladder Cancer
Mitomycin indicated for Gastric Cancer
Mitomycin indicated for Pancreatic Cancer
Mitomycin indicated for Urothelial Cancer
Mitoxantrone Hydrochloride indicated for Acute Myeloid Leukemia
Mitoxantrone Hydrochloride indicated for Prostate Cancer
Mogamulizumab-kpkc indicated for Non-Hodgkin Lymphoma
Monjuvi (Tafasitamab-cxix) indicated for Non-Hodgkin Lymphoma
Moxetumomab Pasudotox-tdfk indicated for Hairy Cell Leukemia
Mozobil (Plerixafor) indicated for Multiple Myeloma
Mozobil (Plerixafor) indicated for Non-Hodgkin Lymphoma
Mvasi (Bevacizumab) indicated for Brain Tumors
Mvasi (Bevacizumab) indicated for Cervical Cancer
Mvasi (Bevacizumab) indicated for Colon Cancer
Mvasi (Bevacizumab) indicated for Non-Small Cell Lung Cancer
Mvasi (Bevacizumab) indicated for Rectal Cancer
Mvasi (Bevacizumab) indicated for Renal Cell Cancer
Myleran (Busulfan) indicated for Chronic Myelogenous Leukemia
Mylotarg (Gemtuzumab Ozogamicin) indicated for Acute Myeloid Leukemia
Naxitamab-gqgk indicated for Brain Tumors
Naxitamab-gqgk indicated for Neuroblastoma
Necitumumab indicated for Non-Small Cell Lung Cancer
Nelarabine indicated for Acute Lymphoblastic Leukemia
Nelarabine indicated for Non-Hodgkin Lymphoma
Neratinib Maleate indicated for Breast Cancer
Nerlynx (Neratinib Maleate) indicated for Breast Cancer
Nexavar (Sorafenib Tosylate) indicated for Liver Cancer
Nexavar (Sorafenib Tosylate) indicated for Renal Cell Cancer
Nexavar (Sorafenib Tosylate) indicated for Thyroid Cancer
Nilandron (Nilutamide) indicated for Prostate Cancer
Nilotinib indicated for Chronic Myelogenous Leukemia
Nilotinib indicated for Myeloproliferative Neoplasms
Nilutamide indicated for Prostate Cancer
Ninlaro (Ixazomib Citrate) indicated for Multiple Myeloma
Niraparib Tosylate Monohydrate indicated for Ovarian Cancer
Nivolumab indicated for Bladder Cancer
Nivolumab indicated for Colon Cancer
Nivolumab indicated for Esophageal Cancer
Nivolumab indicated for Gastric Cancer
Nivolumab indicated for Gastroesophageal Junction Cancer
Nivolumab indicated for Head and Neck Cancer
Nivolumab indicated for Hodgkin Lymphoma
Nivolumab indicated for Liver Cancer
Nivolumab indicated for Malignant Mesothelioma
Nivolumab indicated for Melanoma
Nivolumab indicated for Melanoma
Nivolumab indicated for Non-Small Cell Lung Cancer
Nivolumab indicated for Rectal Cancer
Nivolumab indicated for Renal Cell Cancer
Nivolumab indicated for Small Cell Lung Cancer
Nubeqa (Darolutamide) indicated for Prostate Cancer
Obinutuzumab indicated for Chronic Lymphocytic Leukemia
Obinutuzumab indicated for Non-Hodgkin Lymphoma
Odomzo (Sonidegib) indicated for Basal Cell Carcinoma
Ofatumumab indicated for Chronic Lymphocytic Leukemia
Olaparib indicated for Breast Cancer
Olaparib indicated for Ovarian Cancer
Olaparib indicated for Pancreatic Cancer
Olaparib indicated for Prostate Cancer
Omacetaxine Mepesuccinate indicated for Chronic Myelogenous Leukemia
Oncaspar (Pegaspargase) indicated for Acute Lymphoblastic Leukemia
Onivyde (Irinotecan Hydrochloride Liposome) indicated for Pancreatic Cancer Ontak (Denileukin Diftitox) indicated for Non-Hodgkin Lymphoma
Onureg (Azacitidine) indicated for Acute Myeloid Leukemia
Opdivo (Nivolumab) indicated for Bladder Cancer
Opdivo (Nivolumab) indicated for Colon Cancer
Opdivo (Nivolumab) indicated for Esophageal Cancer
Opdivo (Nivolumab) indicated for Gastric Cancer
Opdivo (Nivolumab) indicated for Gastroesophageal Junction Cancer
Opdivo (Nivolumab) indicated for Head and Neck Cancer
Opdivo (Nivolumab) indicated for Hodgkin Lymphoma
Opdivo (Nivolumab) indicated for Liver Cancer
Opdivo (Nivolumab) indicated for Malignant Mesothelioma
Opdivo (Nivolumab) indicated for Melanoma
Opdivo (Nivolumab) indicated for Melanoma
Opdivo (Nivolumab) indicated for Non-Small Cell Lung Cancer
Opdivo (Nivolumab) indicated for Rectal Cancer
Opdivo (Nivolumab) indicated for Renal Cell Cancer
Opdivo (Nivolumab) indicated for Small Cell Lung Cancer
Orgovyx (Relugolix) indicated for Prostate Cancer
Osimertinib Mesylate indicated for Non-Small Cell Lung Cancer
Oxaliplatin indicated for Colon Cancer
Oxaliplatin indicated for Rectal Cancer
Paclitaxel Albumin-stabilized Nanoparticle Formulation indicated for Breast Cancer
Paclitaxel Albumin-stabilized Nanoparticle Formulation indicated for Non-Small Cell Lung Cancer
Paclitaxel Albumin-stabilized Nanoparticle Formulation indicated for Pancreatic Cancer
Paclitaxel indicated for Breast Cancer
Paclitaxel indicated for Kaposi Sarcoma
Paclitaxel indicated for Non-Small Cell Lung Cancer
Paclitaxel indicated for Ovarian Cancer
Padcev (Enfortumab Vedotin-ejfv) indicated for Bladder Cancer
Palbociclib indicated for Breast Cancer
Pamidronate Disodium indicated for Breast Cancer
Pamidronate Disodium indicated for Multiple Myeloma
Panitumumab indicated for Colon Cancer
Panitumumab indicated for Rectal Cancer
Panobinostat Lactate indicated for Multiple Myeloma
Paraplat (Carboplatin) indicated for Non-Small Cell Lung Cancer
Paraplatin (Carboplatin) indicated for Non-Small Cell Lung Cancer
Pazopanib Hydrochloride indicated for Renal Cell Cancer
Pazopanib Hydrochloride indicated for Soft Tissue Sarcoma
PEG-Intron (Peginterferon Alfa-2b) indicated for Melanoma
Pegaspargase indicated for Acute Lymphoblastic Leukemia
Peginterferon Alfa-2b indicated for Melanoma
Peginterferon Alfa-2b indicated for Melanoma
Pemazyre (Pemigatinib) indicated for Liver Cancer
Pembrolizumab indicated for All Solid Tumors
Pembrolizumab indicated for Bladder Cancer
Pembrolizumab indicated for Breast Cancer
Pembrolizumab indicated for Cervical Cancer
Pembrolizumab indicated for Colon Cancer
Pembrolizumab indicated for Cutaneous Squamous Cell Carcinoma
Pembrolizumab indicated for Endometrial Cancer
Pembrolizumab indicated for Esophageal Cancer
Pembrolizumab indicated for Gastric Cancer
Pembrolizumab indicated for Gastroesophageal Junction Cancer
Pembrolizumab indicated for Head and Neck Cancer
Pembrolizumab indicated for Hodgkin Lymphoma
Pembrolizumab indicated for Liver Cancer
Pembrolizumab indicated for Melanoma
Pembrolizumab indicated for Melanoma
Pembrolizumab indicated for Merkel Cell Carcinoma
Pembrolizumab indicated for Non-Hodgkin Lymphoma
Pembrolizumab indicated for Non-Small Cell Lung Cancer
Pembrolizumab indicated for Rectal Cancer
Pembrolizumab indicated for Renal Cell Cancer
Pemetrexed Disodium indicated for Malignant Mesothelioma
Pemetrexed Disodium indicated for Non-Small Cell Lung Cancer
Pemigatinib indicated for Liver Cancer
Peptaxto (Melphalan Flufenamide Hydrochloride) indicated for Multiple Myeloma
Perj eta (Pertuzumab) indicated for Breast Cancer
Pertuzumab indicated for Breast Cancer
Pertuzumab, Trastuzumab, and Hyaluronidase-zzxf indicated for Breast Cancer
Phesgo (Pertuzumab, Trastuzumab, and Hyaluronidase-zzxf) indicated for Breast Cancer
Piqray (Alpelisib) indicated for Breast Cancer
Plerixafor indicated for Multiple Myeloma
Plerixafor indicated for Non-Hodgkin Lymphoma
Polatuzumab Vedotin-piiq indicated for Non-Hodgkin Lymphoma
Polivy (Polatuzumab Vedotin-piiq) indicated for Non-Hodgkin Lymphoma
Pomalidomide indicated for Kaposi Sarcoma
Pomalidomide indicated for Multiple Myeloma
Pomalyst (Pomalidomide) indicated for Kaposi Sarcoma
Pomalyst (Pomalidomide) indicated for Multiple Myeloma
Ponatinib Hydrochloride indicated for Acute Lymphoblastic Leukemia
Ponatinib Hydrochloride indicated for Chronic Myelogenous Leukemia
Portrazza (Necitumumab) indicated for Non-Small Cell Lung Cancer
Poteligeo (Mogamulizumab-kpkc) indicated for Non-Hodgkin Lymphoma
Pralatrexate indicated for Non-Hodgkin Lymphoma
Pralsetinib indicated for Non-Small Cell Lung Cancer
Pralsetinib indicated for Thyroid Cancer
Prednisone indicated for Acute Lymphoblastic Leukemia
Prednisone indicated for Acute Myeloid Leukemia
Prednisone indicated for Chronic Lymphocytic Leukemia
Prednisone indicated for Hodgkin Lymphoma
Prednisone indicated for Non-Hodgkin Lymphoma
Procarbazine Hydrochloride indicated for Hodgkin Lymphoma
Proleukin (Aldesleukin) indicated for Melanoma
Proleukin (Aldesleukin) indicated for Melanoma
Proleukin (Aldesleukin) indicated for Renal Cell Cancer
Propranolol Hydrochloride indicated for Pheochromocytoma
Provenge (Sipuleucel-T) indicated for Prostate Cancer
Purinethol (Mercaptopurine) indicated for Acute Lymphoblastic Leukemia Purixan (Mercaptopurine) indicated for Acute Lymphoblastic Leukemia
Qinlock (Ripretinib) indicated for Gastrointestinal Stromal Tumors
Radium 223 Dichloride indicated for Prostate Cancer
Ramucirumab indicated for Colon Cancer
Ramucirumab indicated for Gastric Cancer
Ramucirumab indicated for Gastroesophageal Junction Cancer
Ramucirumab indicated for Liver Cancer
Ramucirumab indicated for Non-Small Cell Lung Cancer
Ramucirumab indicated for Rectal Cancer
Recombinant Interferon Alfa-2b indicated for Hairy Cell Leukemia
Recombinant Interferon Alfa-2b indicated for Kaposi Sarcoma
Recombinant Interferon Alfa-2b indicated for Melanoma
Recombinant Interferon Alfa-2b indicated for Melanoma
Recombinant Interferon Alfa-2b indicated for Non-Hodgkin Lymphoma
Regorafenib indicated for Colon Cancer
Regorafenib indicated for Gastrointestinal Stromal Tumors
Regorafenib indicated for Liver Cancer
Regorafenib indicated for Rectal Cancer
Relugolix indicated for Prostate Cancer
Retevmo (Selpercatinib) indicated for Non-Small Cell Lung Cancer
Retevmo (Selpercatinib) indicated for Thyroid Cancer
Revlimid (Lenalidomide) indicated for Multiple Myeloma
Revlimid (Lenalidomide) indicated for Non-Hodgkin Lymphoma
Ribociclib indicated for Breast Cancer
Ripretinib indicated for Gastrointestinal Stromal Tumors
Rituxan (Rituximab) indicated for Chronic Lymphocytic Leukemia
Rituxan (Rituximab) indicated for Non-Hodgkin Lymphoma
Rituxan Hycela (Rituximab and Hyaluronidase Human) indicated for Chronic Lymphocytic Leukemia
Rituxan Hycela (Rituximab and Hyaluronidase Human) indicated for Non-Hodgkin Lymphoma
Rituximab and Hyaluronidase Human indicated for Chronic Lymphocytic Leukemia
Rituximab and Hyaluronidase Human indicated for Non-Hodgkin Lymphoma
Rituximab indicated for Chronic Lymphocytic Leukemia
Rituximab indicated for Non-Hodgkin Lymphoma
Romidepsin indicated for Non-Hodgkin Lymphoma
Rozlytrek (Entrectinib) indicated for All Solid Tumors
Rozlytrek (Entrectinib) indicated for Non-Small Cell Lung Cancer
Rubidomycin (Daunorubicin Hydrochloride) indicated for Acute Lymphoblastic Leukemia
Rubidomycin (Daunorubicin Hydrochloride) indicated for Acute Myeloid Leukemia
Rubidomycin (Daunorubicin Hydrochloride) indicated for Myeloproliferative Neoplasms
Rubraca (Rucaparib Camsylate) indicated for Ovarian Cancer
Rubraca (Rucaparib Camsylate) indicated for Prostate Cancer
Rucaparib Camsylate indicated for Ovarian Cancer
Rucaparib Camsylate indicated for Prostate Cancer
Ruxolitinib Phosphate indicated for Myeloproliferative Neoplasms
Rydapt (Midostaurin) indicated for Acute Myeloid Leukemia
Rydapt (Midostaurin) indicated for Mast Cell Leukemia
Sacituzumab Govitecan-hziy indicated for Bladder Cancer
Sacituzumab Govitecan-hziy indicated for Breast Cancer
Sarclisa (Isatuximab-irfc) indicated for Multiple Myeloma
Selinexor indicated for Multiple Myeloma
Selinexor indicated for Non-Hodgkin Lymphoma
Selpercatinib indicated for Non-Small Cell Lung Cancer
Selpercatinib indicated for Thyroid Cancer
Siltuximab indicated for Multicentric Castleman Disease
Sipuleucel-T indicated for Prostate Cancer
Soltamox (Tamoxifen Citrate) indicated for Breast Cancer
Somatuline Depot (Lanreotide Acetate) indicated for Gastroenteropancreatic Neuroendocrine Tumors
Sonidegib indicated for Basal Cell Carcinoma
Sorafenib Tosylate indicated for Liver Cancer
Sorafenib Tosylate indicated for Renal Cell Cancer
Sorafenib Tosylate indicated for Thyroid Cancer
Sprycel (Dasatinib) indicated for Acute Lymphoblastic Leukemia
Sprycel (Dasatinib) indicated for Chronic Myelogenous Leukemia
Sprycel (Dasatinib) indicated for Myeloproliferative Neoplasms
Stivarga (Regorafenib) indicated for Colon Cancer
Stivarga (Regorafenib) indicated for Gastrointestinal Stromal Tumors
Stivarga (Regorafenib) indicated for Liver Cancer
Stivarga (Regorafenib) indicated for Rectal Cancer
Sunitinib Malate indicated for Gastrointestinal Stromal Tumors
Sunitinib Malate indicated for Pancreatic Cancer
Sunitinib Malate indicated for Renal Cell Cancer
Sutent (Sunitinib Malate) indicated for Gastrointestinal Stromal Tumors
Sutent (Sunitinib Malate) indicated for Pancreatic Cancer
Sutent (Sunitinib Malate) indicated for Renal Cell Cancer
Sylatron (Peginterferon Alfa-2b) indicated for Melanoma
Sylatron (Peginterferon Alfa-2b) indicated for Melanoma
Sylvant (Siltuximab) indicated for Multicentric Castleman Disease
Synribo (Omacetaxine Mepesuccinate) indicated for Chronic Myelogenous Leukemia
Tabloid (Thioguanine) indicated for Acute Myeloid Leukemia
Tabrecta (Capmatinib Hydrochloride) indicated for Non-Small Cell Lung Cancer
Tafasitamab-cxix indicated for Non-Hodgkin Lymphoma
Tafinlar (Dabrafenib Mesylate) indicated for Melanoma
Tafinlar (Dabrafenib Mesylate) indicated for Non-Small Cell Lung Cancer
Tafinlar (Dabrafenib Mesylate) indicated for Thyroid Cancer
Tafinlar (Dabrafenib) indicated for Melanoma
Tagraxofusp-erzs indicated for Blastic Plasmacytoid Dendritic Cell Neoplasm
Tagrisso (Osimertinib Mesylate) indicated for Non-Small Cell Lung Cancer
Talazoparib Tosylate indicated for Breast Cancer
Talimogene Laherparepvec indicated for Melanoma
Talimogene Laherparepvec indicated for Melanoma
Talzenna (Talazoparib Tosylate) indicated for Breast Cancer
Tamoxifen Citrate indicated for Breast Cancer Tarabine PFS (Cytarabine) indicated for Myeloproliferative Neoplasms
Tarceva (Erlotinib Hydrochloride) indicated for Non-Small Cell Lung Cancer
Tarceva (Erlotinib Hydrochloride) indicated for Pancreatic Cancer
Tasigna (Nilotinib) indicated for Chronic Myelogenous Leukemia
Tasigna (Nilotinib) indicated for Myeloproliferative Neoplasms
Taxotere (Docetaxel) indicated for Breast Cancer
Taxotere (Docetaxel) indicated for Gastric Cancer
Taxotere (Docetaxel) indicated for Gastroesophageal Junction Cancer
Taxotere (Docetaxel) indicated for Head and Neck Cancer
Taxotere (Docetaxel) indicated for Non-Small Cell Lung Cancer
Taxotere (Docetaxel) indicated for Prostate Cancer
Tazemetostat Hydrobromide indicated for Non-Hodgkin Lymphoma
Tazemetostat Hydrobromide indicated for Soft Tissue Sarcoma
Tazverik (Tazemetostat Hydrobromide) indicated for Non-Hodgkin Lymphoma
Tazverik (Tazemetostat Hydrobromide) indicated for Soft Tissue Sarcoma
Tecartus (Brexucabtagene Autoleucel) indicated for Non-Hodgkin Lymphoma
Tecentriq (Atezolizumab) indicated for Bladder Cancer
Tecentriq (Atezolizumab) indicated for Breast Cancer
Tecentriq (Atezolizumab) indicated for Liver Cancer
Tecentriq (Atezolizumab) indicated for Non-Small Cell Lung Cancer
Tecentriq (Atezolizumab) indicated for Small Cell Lung Cancer
Temodar (Temozolomide) indicated for Brain Tumors
Temozolomide indicated for Brain Tumors
Temsirolimus indicated for Renal Cell Cancer
Tepadina (Thiotepa) indicated for Bladder Cancer
Tepadina (Thiotepa) indicated for Breast Cancer
Tepadina (Thiotepa) indicated for Ovarian Cancer
Tepmetko (Tepotinib Hydrochloride) indicated for Non-Small Cell Lung Cancer
Tepotinib Hydrochloride indicated for Non-Small Cell Lung Cancer
Thalidomide indicated for Multiple Myeloma
Thalomid (Thalidomide) indicated for Multiple Myeloma
Thioguanine indicated for Acute Myeloid Leukemia
Thiotepa indicated for Bladder Cancer
Thiotepa indicated for Breast Cancer
Thiotepa indicated for Ovarian Cancer
Tibsovo (Ivosidenib) indicated for Acute Myeloid Leukemia
Tisagenlecleucel indicated for Acute Lymphoblastic Leukemia
Tisagenlecleucel indicated for Non-Hodgkin Lymphoma
Tivozanib Hydrochloride indicated for Renal Cell Cancer
Topotecan Hydrochloride indicated for Cervical Cancer
Topotecan Hydrochloride indicated for Ovarian Cancer
Topotecan Hydrochloride indicated for Small Cell Lung Cancer
Toremifene indicated for Breast Cancer
Torisel (Temsirolimus) indicated for Renal Cell Cancer
Trabectedin indicated for Soft Tissue Sarcoma
Trametinib Dimethyl Sulfoxide indicated for Melanoma
Trametinib Dimethyl Sulfoxide indicated for Melanoma
Trametinib Dimethyl Sulfoxide indicated for Non-Small Cell Lung Cancer
Trametinib Dimethyl Sulfoxide indicated for Thyroid Cancer
Trastuzumab and Hyaluronidase-oysk indicated for Breast Cancer
Trastuzumab indicated for Breast Cancer
Trastuzumab indicated for Gastric Cancer
Trastuzumab indicated for Gastroesophageal Junction Cancer
Treanda (Bendamustine Hydrochloride) indicated for Chronic Lymphocytic Leukemia
Treanda (Bendamustine Hydrochloride) indicated for Non-Hodgkin Lymphoma
Trexall (Methotrexate Sodium) indicated for Acute Lymphoblastic Leukemia
Trexall (Methotrexate Sodium) indicated for Bone Cancer
Trexall (Methotrexate Sodium) indicated for Breast Cancer
Trexall (Methotrexate Sodium) indicated for Gestational Trophoblastic Disease
Trexall (Methotrexate Sodium) indicated for Head and Neck Cancer
Trexall (Methotrexate Sodium) indicated for Non-Hodgkin Lymphoma
Trexall (Methotrexate Sodium) indicated for Non-Small Cell Lung Cancer
Trexall (Methotrexate Sodium) indicated for Small Cell Lung Cancer
Trifluridine and Tipiracil Hydrochloride indicated for Colon Cancer
Trifluridine and Tipiracil Hydrochloride indicated for Gastric Cancer
Trifluridine and Tipiracil Hydrochloride indicated for Gastroesophageal Junction Cancer
Trifluridine and Tipiracil Hydrochloride indicated for Rectal Cancer
Trisenox (Arsenic Trioxide) indicated for Acute Myeloid Leukemia
Trisenox (Arsenic Trioxide) indicated for Myeloproliferative Neoplasms
Trodelvy (Sacituzumab Govitecan-hziy) indicated for Bladder Cancer
Trodelvy (Sacituzumab Govitecan-hziy) indicated for Breast Cancer
Truxima (Rituximab) indicated for Chronic Lymphocytic Leukemia
Truxima (Rituximab) indicated for Non-Hodgkin Lymphoma
Tucatinib indicated for Breast Cancer
Tukysa (Tucatinib) indicated for Breast Cancer
Tykerb (Lapatinib Ditosylate) indicated for Breast Cancer
Ukoniq (Umbralisib Tosylate) indicated for Non-Hodgkin Lymphoma
Umbralisib Tosylate indicated for Non-Hodgkin Lymphoma
Unituxin (Dinutuximab) indicated for Neuroblastoma
Valrubicin indicated for Bladder Cancer
Valstar (Valrubicin) indicated for Bladder Cancer
Vandetanib indicated for Thyroid Cancer
Vectibix (Panitumumab) indicated for Colon Cancer
Vectibix (Panitumumab) indicated for Rectal Cancer
Velcade (Bortezomib) indicated for Multiple Myeloma
Velcade (Bortezomib) indicated for Non-Hodgkin Lymphoma
Vemurafenib indicated for Melanoma
Vemurafenib indicated for Melanoma Venclexta (Venetoclax) indicated for Acute Myeloid Leukemia
Venclexta (Venetoclax) indicated for Chronic Lymphocytic Leukemia
Venclexta (Venetoclax) indicated for Non-Hodgkin Lymphoma
Venetoclax indicated for Acute Myeloid Leukemia
Venetoclax indicated for Chronic Lymphocytic Leukemia
Venetoclax indicated for Non-Hodgkin Lymphoma
Verzenio (Abemaciclib) indicated for Breast Cancer
Vidaza (Azacitidine) indicated for Myeloproliferative Neoplasms
Vinblastine Sulfate indicated for Breast Cancer
Vinblastine Sulfate indicated for Gestational Trophoblastic Disease
Vinblastine Sulfate indicated for Hodgkin Lymphoma
Vinblastine Sulfate indicated for Kaposi Sarcoma
Vinblastine Sulfate indicated for Non-Hodgkin Lymphoma
Vinblastine Sulfate indicated for Testicular Cancer
Vincristine Sulfate indicated for Acute Lymphoblastic Leukemia
Vincristine Sulfate indicated for Acute Myeloid Leukemia
Vincristine Sulfate indicated for Childhood Kidney Cancers
Vincristine Sulfate indicated for Hodgkin Lymphoma
Vincristine Sulfate indicated for Neuroblastoma
Vincristine Sulfate indicated for Non-Hodgkin Lymphoma
Vincristine Sulfate indicated for Rhabdomyosarcoma
Vincristine Sulfate Liposome indicated for Acute Lymphoblastic Leukemia
Vinorelbine Tartrate indicated for Non-Small Cell Lung Cancer
Vismodegib indicated for Basal Cell Carcinoma
Vitrakvi (Larotrectinib Sulfate) indicated for All Solid Tumors
Vizimpro (Dacomitinib) indicated for Non-Small Cell Lung Cancer
Vorinostat indicated for Non-Hodgkin Lymphoma
Votrient (Pazopanib Hydrochloride) indicated for Renal Cell Cancer
Votrient (Pazopanib Hydrochloride) indicated for Soft Tissue Sarcoma
Vyxeos (Daunorubicin Hydrochloride and Cytarabine Liposome) indicated for Acute Myeloid Leukemia
Xalkori (Crizotinib) indicated for Non-Hodgkin Lymphoma
Xalkori (Crizotinib) indicated for Non-Small Cell Lung Cancer
Xeloda (Capecitabine) indicated for Breast Cancer
Xeloda (Capecitabine) indicated for Colon Cancer
Xeloda (Capecitabine) indicated for Rectal Cancer
Xgeva (Denosumab) indicated for Bone Cancer
Xofigo (Radium 223 Dichloride) indicated for Prostate Cancer
Xospata (Gilteritinib Fumarate) indicated for Acute Myeloid Leukemia
Xpovio (Selinexor) indicated for Multiple Myeloma
Xpovio (Selinexor) indicated for Non-Hodgkin Lymphoma
Xtandi (Enzalutamide) indicated for Prostate Cancer
Yervoy (Ipilimumab) indicated for Colon Cancer
Yervoy (Ipilimumab) indicated for Malignant Mesothelioma
Yervoy (Ipilimumab) indicated for Melanoma
Yervoy (Ipilimumab) indicated for Melanoma
Yervoy (Ipilimumab) indicated for Non-Small Cell Lung Cancer
Yervoy (Ipilimumab) indicated for Rectal Cancer
Yervoy (Ipilimumab) indicated for Renal Cell Cancer
Yescarta (Axicabtagene Ciloleucel) indicated for Non-Hodgkin Lymphoma
Yondelis (Trabectedin) indicated for Soft Tissue Sarcoma
Yonsa (Abiraterone Acetate) indicated for Prostate Cancer
Zaltrap (Ziv-Aflibercept) indicated for Colon Cancer
Zaltrap (Ziv-Aflibercept) indicated for Rectal Cancer
Zanubrutinib indicated for Non-Hodgkin Lymphoma
Zejula (Niraparib Tosylate Monohydrate) indicated for Ovarian Cancer
Zelboraf (Vemurafenib) indicated for Melanoma
Zelboraf (Vemurafenib) indicated for Melanoma
Zepzelca (Lurbinectedin) indicated for Small Cell Lung Cancer
Zevalin (Ibritumomab Tiuxetan) indicated for Non-Hodgkin Lymphoma
Zirabev (Bevacizumab) indicated for Brain Tumors
Zirabev (Bevacizumab) indicated for Cervical Cancer
Zirabev (Bevacizumab) indicated for Colon Cancer
Zirabev (Bevacizumab) indicated for Non-Small Cell Lung Cancer
Zirabev (Bevacizumab) indicated for Rectal Cancer
Zirabev (Bevacizumab) indicated for Renal Cell Cancer
Ziv-Aflibercept indicated for Colon Cancer
Ziv-Aflibercept indicated for Rectal Cancer
Zoladex (Goserelin Acetate) indicated for Breast Cancer
Zoladex (Goserelin Acetate) indicated for Prostate Cancer
Zoledronic Acid indicated for Bone Cancer
Zoledronic Acid indicated for Multiple Myeloma
Zolinza (Vorinostat) indicated for Non-Hodgkin Lymphoma
Zometa (Zoledronic Acid) indicated for Multiple Myeloma
Zometa indicated for Bone Cancer
Zydelig (Idelalisib) indicated for Chronic Lymphocytic Leukemia
Zydelig (Idelalisib) indicated for Non-Hodgkin Lymphoma
Zykadia (Ceritinib) indicated for Non-Small Cell Lung Cancer
Zynlonta (Loncastuximab Tesirine-lpyl) indicated for Non-Hodgkin Lymphoma
Zytiga (Abiraterone Acetate) indicated for Prostate Cancer Side Effects Associated with Combination Cancer Treatments:
ABVD (Adriamycin, Bleomycin, Vinblasine, Dacarbazine indicated for Hodgkin Lymphoma
ABVE (Adriamycin, Bleomycin, Vincristine Sulfate, Etoposide Phosphate) indicated for Hodgkin Lymphoma
ABVE-PC (Adriamycin, Bleomycin, Vincristine Sulfate, Etoposide Phosphate, Prednisone, Cyclophosphamide) indicated for Hodgkin Lymphoma
AC (Adriamycin, Cyclophosphamide) indicated for Breast Cancer
AC-T (Adriamycin, Cyclophosphamide, Taxol) indicated for Breast Cancer
ADE (Cytarabine, Daunorubicine Hydrochloride, Etoposide Phosphate) indicated for Acute Myeloid Leukemia
ADE (Cytarabine, Daunorubicine Hydrochloride, Etoposide Phosphate) indicated for Myeloproliferative Neoplasms BEACOPP (Bleomycin, Etoposide, Adriamycin, Cyclophosphamide, Oncovin, Procarbazine, Prednisone) indicated for Hodgkin Lymphoma BEP (Bleomycin, Etoposide, Cisplatin) indicated for Ovarian Cancer BEP (Bleomycin, Etoposide, Cisplatin) indicated for Testicular Cancer BuMel (Busulfan, Melphalan Hysrochloride) indicated for Neuroblastoma CAF (Cyclophosphamide, Adriamycin, Fluorouracil) indicated for Breast Cancer CAPDX (Capecitabine, Oxaliplatin) indicated for Colon Cancer CAPDX (Capecitabine, Oxaliplatin) indicated for Rectal Cancer CARBOPLATIN-TAXOL (Carboplatin, Paclitaxel) indicated for Non-Small Cell Lung Cancer CARBOPLATIN-TAXOL (Carboplatin, Paclitaxel) indicated for Ovarian Cancer CEM (Carboplatin, Etoposide Phosphate, Melphalan Hydrochloride) indicated for Neuroblastoma CEV (Carboplatin, Etoposide Phosphate, Vincristine Sulfate) indicated for Retinoblastoma CHLORAMBUCIL-PREDNISONE indicated for Chronic Lymphocytic Leukemia CHOP (Cyclophosphamide, Doxorubicin Hydrochloride, Vincristine Sulfate (Onvocin), Prednisone) indicated for Non-Hodgkin Lymphoma CMF (Cyclophosphamide, Methotrexate, Fluorouracil) indicated for Breast Cancer COPDAC (Cyclophosphamide, Vincristine Sulfate (Oncovin), Prednisone, Dacarbazine) indicated for Hodgkin Lymphoma COPP (Cyclophosphamide, Vincristine Sulfate (Oncovin), Procarbazine Hydrochloride, Prednisone) indicated for Hodgkin Lymphoma COPP (Cyclophosphamide, Vincristine Sulfate (Oncovin), Procarbazine Hydrochloride, Prednisone) indicated for Non-Hodgkin Lymphoma COPP-ABV ((Cyclophosphamide, Vincristine Sulfate (Oncovin), Procarbazine Hydrochloride, Prednisone, Adriamycin, Bleomycin, Vinblastine Sulfate) indicated for Hodgkin Lymphoma CVP (Cyclophosphamide, Vincristine Sulfate, Prednisone) indicated for Chronic Lymphocytic Leukemia CVP (Cyclophosphamide, Vincristine Sulfate, Prednisone) indicated for Non-Hodgkin Lymphoma EPOCH (Etoposide Phosphate, Prednisone, Vincristine Sulfate (Oncovin), Cyclophosphamide, Doxorubicin Hydrochloride (Hydroxydaunomycin) indicated for Non-Hodgkin Lymphoma FEC (Fluorouracil, Epirubicin Hydrochloride, Cyclophosphamide) indicated for Breast Cancer FOLFIRI (Leucovorin Calcium (Folinic Acid), Fluorouracil, Irinotecan Hydrochloride) indicated for Colon Cancer FOLFIRI (Leucovorin Calcium (Folinic Acid), Fluorouracil, Irinotecan Hydrochloride) indicated for Rectal Cancer FOLFIRI-BEVACIZUMAB (Leucovorin Calcium (Folinic Acid), Fluorouracil, Irinotecan Hydrochloride, Bevacizumab) indicated for Colon Cancer FOLFIRI-BEVACIZUMAB (Leucovorin Calcium (Folinic Acid), Fluorouracil, Irinotecan Hydrochloride, Bevacizumab) indicated for Rectal Cancer FOLFIRI-CETUXIMAB (Leucovorin Calcium (Folinic Acid), Fluorouracil, Irinotecan Hydrochloride, Cetuximab) indicated for Colon Cancer FOLFIRI-CETUXIMAB (Leucovorin Calcium (Folinic Acid), Fluorouracil, Irinotecan Hydrochloride, Cetuximab) indicated for Rectal Cancer FOLFIRINOX (Leucovorin Calcium (Folinic Acid), Fluorouracil, Irinotecan Hydrochloride, Oxaliplatin) indicated for Pancreatic Cancer FOLFOX (Leucovorin Calcium (Folinic Acid), Fluorouracil, Oxaliplatin) indicated for Colon Cancer FOLFOX Leucovorin Calcium (Folinic Acid), Fluorouracil, Oxaliplatin) indicated for Rectal Cancer FU-LV (Fluorouracil, Leucovorin Calcium) indicated for Colon Cancer FU-LV (Fluorouracil, Leucovorin Calcium) indicated for Esophageal Cancer FU-LV (Fluorouracil, Leucovorin Calcium) indicated for Gastric Cancer FU-LV (Fluorouracil, Leucovorin Calcium) indicated for Rectal Cancer GEMCITABINE-CISPLATIN indicated for Bladder Cancer Gemcitabine-Cisplatin indicated for Cervical Cancer GEMCITABINE-CISPLATIN indicated for Malignant Mesothelioma GEMCITABINE-CISPLATIN indicated for Non-Small Cell Lung Cancer GEMCITABINE-CISPLATIN indicated for Ovarian Cancer GEMCITABINE-CISPLATIN indicated for Pancreatic Cancer GEMCITABINE-OXALIPLATIN indicated for Pancreatic Cancer Hyper-CVAD (Cyclophosphamide, Vincristine Sulfate, Doxorubicin Hydrochloride (Adriamycin) Dexamethasone) indicated for Acute Lymphoblastic Leukemia Hyper-CVAD (Cyclophosphamide, Vincristine Sulfate, Doxorubicin Hydrochloride (Adriamycin) Dexamethasone) indicated for Non-Hodgkin Lymphoma ICE (Ifosfamide, Carboplatin, Etoposide Phosphate) indicated for Hodgkin Lymphoma ICE (Ifosfamide, Carboplatin, Etoposide Phosphate) indicated for Non-Hodgkin Lymphoma JEB (Carboplatin (JM8), Etoposide Phosphate, Bleomycin) indicated for Ovarian Cancer JEB (Carboplatin (JM8), Etoposide Phosphate, Bleomycin) indicated for Testicular Cancer MOPP (Mechlorethamine Hydrochloride, Vincristine Sulfate (Oncovin), Procarbazine Hydrochloride, Prednisone) indicated for Hodgkin Lymphoma MVAC (Methotrexate, Vinblastine Sulfate, Doxorubicin Hydrochloride (Adriamycin), Cisplatin) indicated for Bladder Cancer OEPA (Vincristine Sulfate (Oncovin), Etoposide Phosphate, Prednisone, Doxorubicin Hydrochloride (Adriamycin)) indicated for Hodgkin Lymphoma OFF (Oxaliplatin, Fluorouracil, Leucovorin Calcium (Folinic Acid)) indicated for Pancreatic Cancer OPPA (Vincristine Sulfate (Oncovin), Procarbazine Hydrochloride, Prednisone, Doxorubicin Hydrochloride (Adriamycin)) indicated for Hodgkin Lymphoma PAD (Bortezomib (PS-341), Doxorubicin Hydrochloride (Adriamycin), Dexamethasone) indicated for Multiple Myeloma PCV (Procarbazine Hydrochloride, Lomustine (CCNU), Vincristine Sulfate) indicated for Brain Tumors PEB (Cisplatin (Platinol), Etoposide Phosphate, Bleomycin) indicated for Ovarian Cancer PEB (Cisplatin (Platinol), Etoposide Phosphate, Bleomycin) indicated for Testicular Cancer R-CHOP (Rituximab, Cyclophosphamide, Doxorubicin Hydrochloride, Vincristine Sulfate (Onvocin), Prednisone) indicated for Non-Hodgkin Lymphoma R-CVP (Rituximab, Cyclophosphamide, Vincristine Sulfate, Prednisone) indicated for Non-Hodgkin Lymphoma R-EPOCH (Rituximab, Etoposide Phosphate, Prednisone, Vincristine Sulfate (Oncovin), Cyclophosphamide, Doxorubicin Hydrochloride (Hydroxydaunomycin)) indicated for Non-Hodgkin Lymphoma R-ICE (Rituximab, Ifosfamide, Carboplatin, Etoposide Phosphate) indicated for Non-Hodgkin Lymphoma STANFORD V (Mechlorethamine Hydrochloride, Doxorubicin Hydrochloride, Vinblastine Sulfate, Vincristine Sulfate, Bleomycin, Etoposide Phosphate, Prednisone) indicated for Hodgkin Lymphoma TAC (Docetaxel (Taxotere), Doxorubicin Hydrochloride (Adriamycin), Cyclophosphamide) indicated for Breast Cancer TPF (Docetaxel (Taxotere), Cisplatin (Platinol), Fluorouracil) indicated for Gastric Cancer TPF (Docetaxel (Taxotere), Cisplatin (Platinol), Fluorouracil) indicated for Head and Neck Cancer VAC (Vincristine Sulfate, Dactinomycin (Actinomycin-D), Cyclophosphamide) indicated for Ovarian Cancer VAC (Vincristine Sulfate, Dactinomycin (Actinomycin-D), Cyclophosphamide) indicated for Soft Tissue Sarcoma VAMP (Vincristine Sulfate, Doxorubicin Hydrochloride (Adriamycin), Methotrexate, Prednisone) indicated for Hodgkin Lymphoma VeIP (Vinblastine Sulfate (Velban), Ifosfamide, Cisplatin (Platinol)) indicated for Ovarian Cancer VeIP (Vinblastine Sulfate (Velban), Ifosfamide, Cisplatin (Platinol)) indicated for Testicular Cancer VIP (Eroposide (VP-16), Ifosfamide, Cisplatin (Platinol)) indicated for Testicular Cancer XELIRI (Capecitabine (Xeloda), Irinotecan Hydrochloride) indicated for Colon Cancer XELIRI (Capecitabine (Xeloda), Irinotecan Hydrochloride) indicated for Esophageal Cancer XELIRI (Capecitabine (Xeloda), Irinotecan Hydrochloride) indicated for Gastric Cancer XELIRI (Capecitabine (Xeloda), Irinotecan Hydrochloride) indicated for Rectal Cancer XELOX (Capecitabine (Xeloda), Oxaliplatin) indicated for Colon Cancer XELOX (Capecitabine (Xeloda), Oxaliplatin) indicated for Rectal Cancer While the above mentioned drugs are useful in treating cancer, such drugs produce significant side effects.

Medication induced side effects of chemotheraphy in a patient are related to the side effect of chemotherapy on rapidly dividing cells in addition to cancer cells. Some side effects are annoying and uncomfortable. Other side effects are dangerous and even life threatening. Chemotherapy side effects include Actinic Keratosis; Aggressive Systemic Mastocytosis; Acnemia (Low Red Blood Cells); Cacinoid Syndrome; Cardiac Toxicity; Condyloma Acuminatum (Genital Wards); Constipation; Cytokine Release Syndrome; Drug Extravasation (Drug Leakage in Tissues); Hemorrhage Cystitis (Bleeding in the Bladder); Hepatic Veno-occlusive Disease (Blocked Liver Veins); Hepatitis C Infection; Hypercalcemia of Malignancy (High Blood Calcium); Malignant Effusions; Mucositis (Inflamed Mucous Membranes); Nausea and Vomitting; Nerotoxicity (Nervous System Side Effects); Neutopenia (Low Blood Neutophils); Osteoporosis (Low Bone Density); Renal Toxicity (Kidney Side Effects); Skin Changes Due to Cutaneous Metastases; sepsis; Thrombocytopenia (Low Blood Platelets); Tumor Lysis Syndrome (Cell Breakdown and Organ Damage); and Chemotherapy Induced Febrile Neutopenia. Like a canary in a mine, certain parameters such as Chemotherapy induced Febrile Neutopenia, cytokine release storm, sepsis, changes in EKG, EEG, respiration, etc., are often early indications of adverse side effects. In particular, by sensing and recording changes in a patient's selected parameters, early intervention, e.g., through administration of oral antibiotics and/or a change in drug regiment may be prescribed.

The present invention relates to a system, i.e. method and apparatus for out-patient monitoring of development of medication induced side effects in a patient. The invention has particular utility in connection with the out-patient monitoring of chemotherapy induced febrile neutropenia, and will be described in connection with such utility, although other utilities are contemplated.

Immune dysregulation is a component of many pathological diseases or conditions. Such dysregulation may be a factor that favors the establishment, maintenance or progression of diseases or conditions. Immune response or immune suppression also frequently results from medication treatments including specifically chemotherapy that is used in the treatment of cancer.

Outpatient therapy for low-risk neutropenic patients is considered safe, but remains an uncommon practice. However, even with regular monitoring, including frequent in-office or outpatient monitoring, patients frequently get into trouble resulting in costly hospitalizations for treatment of chemotheraphy induced febrile neutropenia, since by the time the patient is diagnosed, it often is too late for treatment other than through administration of paranteral antibiotics.

Although the definition for chemotherapy induced febrile neutropenia vary across institutions and guidelines, most North American Societies define a single oral temperature of >38.3° C. (101.3° F.) or a temperature of >38° C. (100.4° F.) sustained for >1 hour as significant and neutropenia with an ANC<1000 cells/microL, whilst severe neutropenia is considered an absolute neutrophil count (ANC)<500 cells/microL, or an ANC that is expected to decrease to <500 cells/microL over the next 48 hours[1]. In spite of the wide utilization of growth factors and prophylactic antimicrobial therapy in patients obtaining chemotherapy for their malignant disease, febrile neutropenia still remains a common treatment related complication[2]. Early studies linked infections in the context of severe neutropenia with a substantial mortality rate[3].

The corresponding concern of the development of an overwhelming sepsis episode rendered hospitalization with the administration of parenteral antibiotics as the standard of care in the management of patients with febrile neutropenia for many decades. It is now well recognized that neutropenic fever patients represent a very heterogeneous group[4]. The Multinational Association for the Supportive Care in Cancer (MASCC) proposed a seven point model, consisting of (1) degree of symptom burden, (2) presence or absence of hypotension, (3) need for IV fluid resuscitation, (4) presence or absence of COPD as a comorbidity, (5) solid tumor malignancy or hematologic malignancy without prior fungal infection, (6) outpatient status and (7) age above or below sixty years old as relevant clinico-demographic cofactors for the risk stratification of patients presenting with chemotherapy induced febrile neutropenia[4]. At least seven randomized trials have established the use of outpatient antibiotics as a safe and efficacious strategy in low risk febrile neutropenia[5-11]. In addition, the comparability of oral with intravenous regimens has been demonstrated[12-15]. Several guidelines support the use of outpatient antibiotics in the low risk setting[16-18]. A recent systematic review with meta-analysis revealed equal mortality with inpatient versus outpatient therapy with comparables rates of treatment failure[2]. Benefits of outpatient therapy in this setting include increased patient acceptance and the absence of exposure to a nosocomial environment. In addition, recent health economic comparisons of inpatient versus outpatient therapy in the low risk neutropenic feversetting have demonstrated striking savings with outpatient therapy[19,20].

In spite of the available feasibility data and the benefits of outpatient therapy vs inpatient therapy described above, a large amount of patients with chemotherapy associated neutropenic fever are still admitted to the hospital for parenteral IV antibiotic therapy for the full length of their neutropenic presentation. A major reason for this is concern of further deterioration following the initial assessment at presentation.

SUMMARY OF THE INVENTION

The present invention provides a remote monitoring solution which permits out-patient early detection of chemotherapy associated febrile neutropenia and other early indications of adverse side effects, such as cytokine release storm, sepsis, pneumonitis, neurotoxicity, gastrointestinal toxicities, etc., and which often permits patients to be safely cared for in their own home environment, i.e. by early administration of oral antibiotics. An integrated algorithm captures early signs of deterioration, which might otherwise lead to hospitalization of the patient, and alerts the patient and medical personnel to begin administration or oral antibiotics before clinical characteristics render the patient a high-risk patient requiring hospitalization.

The multinational association for the supportive care in cancer patients (MASCC) proposes a weighted seven variable algorithm for the clinic-demographic assessment of a patient with chemotherapy related neutropenic fever[4]:
(1) degree of symptom burden
(2) presence or absence of hypotension
(3) need for IV fluid resuscitation
(4) presence or absence of COPD as a comorbidity
(5) solid tumor malignancy or hematologic malignancy without prior fungal infection
(6) outpatient status
(7) age, i.e. above or below sixty years old However, other, in certain aspects simpler algorithms have been proposed. The Infectious Diseases Society of America (IDSA) has proposed a ten point algorithm to stratify a patient with chemotherapy related febrile neutropenia as high or low risk. Any of the following clinical characteristics renders the patient as a high-risk patient[1].
1. ANC≤100 cells/microL expected to last >7 days
2. Hemodynamic instability
3. Oral or gastrointestinal tract mucositis limiting swallowing or causing severe diarrhea
4. Gastrointestinal symptoms, such as abdominal pain, nausea and vomiting, or diarrhea
5. Neurologic or mental status changes of new onset
6. Intravascular catheter infection
7. New pulmonary infiltrate or hypoxia
8. Underlying chronic lung disease
9. Evidence of hepatic insufficiency (defined as aminotransferase levels >5 times normal values)
10. renal insufficiency (defined as a creatinine clearance <30 mL/min In addition, the National Comprehensive Cancer Network (NCCN) proposes a more detailed breakdown of patients with chemotherapy related febrile neutropenia as high, intermediate or low risk[21].

In addition to including an intermediate risk strata, the NCCN also includes the exposure to certain heavily immune-compromising anti-neoplastic agents (such as alemtuzumab) as risk factors.

High-Risk—the NCCN Categorizes Febrile Neutropenic Patients as High-Risk if any of the Following Criteria are Met:
  Inpatient status at time of development of fever
  Significant medical comorbidity or presence of clinical instability
  Anticipated prolonged profound neutropenia (ANC≤100 cells/microL expected to last >7 days)
  Hepatic insufficiency (defined as aminotransferase levels >5 times normal values) or renal insufficiency (defined as a creatinine clearance <30 mL/min)
  Uncontrolled progressive cancer defined as any leukemic patient not in complete remission, or any non-leukemic patient with evidence of disease progression after more than two courses of chemotherapy
  Pneumonia or other complex infection at clinical presentation
  Alemtuzumab exposure within the past two months
  Grade 3 or 4 mucositis
  Multinational Association for Supportive Care in Cancer (MAS CC) risk index score
  <21

Intermediate risk—In addition to the categories of high-risk and low-risk described above, the NCCN defines febrile neutropenic patients to be intermediate-risk for complications if any of the following criteria are met:
  Autologous HCT
  Lymphoma
  Chronic lymphocytic leukemia
  Multiple myelorna
  Purine analog therapy
  Anticipated duration of neutropenia of 7 to 10 days Low-risk—The NCCN categorizes febrile neutropenic patients as low-risk for complications if they do not meet any of the high-risk criteria described above and if they meet most of the following criteria:
  Outpatient status at time of development of fever
  No associated acute comorbid illness requiring inpatient hospitalization or close observation
  Anticipated short duration of severe neutropenia (ANC≤100 cells/microL expected to last 7 days or fewer)
  Good performance status (Eastern Cooperative Oncology Group ~ECOG1 0-1
  No hepatic insufficiency
  No renal insufficiency
  Multinational Association for Supportive Care in Cancer (MASCC) risk index score
  ≥21

The present invention provides a system involving both hardware and software tools for monitoring and measuring a patient's health, and for assessing a change in a patient's condition, changing his/her risk status and the corresponding clinical approach.

Embodiments of the present disclosure provide systems and methods for home monitoring and detection of febrile neutropenia and/or monitoring and detection of other physical markers such as electrocardiographic parameters, respiration, etc., in a patient. Briefly described, in architecture, one embodiment of a system, among others, can be implemented as follows. The system includes a wearable photoplethysmographic sensor for sensing photoplethysmographic signals of the patient, and/or one or more blood borne parameter sensors for sensing parameters in the patient's blood, and/or one or more other sensors for measuring other physical markers of the patient. A patient monitoring application is hosted at least partially on a server and electronically accessible over at least one network system to a patient computer. The patient monitoring application is configured to receive information sensed by the physical sensor(s) and to determine, based on the received information, the presence or deterioration of a patient deteriorating condition.

In one embodiment, the system comprises a photoplemysmography sensor and a wearable movement sensor for sensing movement of the patient, wherein the photoplethysmographic signals are corrected based on information sensed by the movement sensor, In another embedment, the system further comprises a healthcare provider computer, wherein the patient monitoring application is further configured to provide an alarm to the healthcare provider computer upon a determination of the presence or deterioration of febrile neutropenia in the patient.

In one embodiment, the patient monitoring application is further configured to provide an alarm to the healthcare provider computer upon a determination of patient non-compliance with a patient monitoring protocol.

In yet another embodiment the system further comprises a temperature sensor for sensing the patient's body temperature, wherein the patient monitoring application is further configured to receive information sensed by the temperature sensor and to determine the presence or deterioration of febrile neutropenia based at least in part on the sensed temperature information.

In still yet another embodiment, the system further comprises at least one of a sensor for measuring blood pressure and/or heart rate and/or pulse oxygen %, i.e., a pulse oximeter, and optinally a scale for measuring the patient's weight, wherein the febrile neutropenia monitoring application is configured to receive information sensed by the at least one of a blood pressure and/or heart rate and/or pulse ox, sensor and scale and to determine the presence or deterioration of febrile neutropenia based at least in part on the information sensed by the at least one of a blood pressure and/or heart rate and/or pulse ox sensor and scale.

In one embodiment the patient monitoring application is further configured to determine and monitor the patient's peripheral vascular resistance and heart rate based on the information sensed by the photoplethysmographic sensor, and/or to determine and monitor the patient's breathing rate, breathing depth and optionally a spirometer for measuring the patient's spironometric values, i.e., lung volume.

In yet another embodiment the patient monitoring sensors comprise blood borne parameter sensors for sensing or counting at least one of neutrophils and monocytes.

In still yet another embodiment the patient monitoring sensors comprise a multiplex biochemical assay for detecting at least one of: interleukin 1 and 6; tumor necrosis factor; procalcitonin; and C-reactive protein.

In yet another embodiment the patient monitoring application is further configured to provide a communication to the patient computer, upon a determination of the presence or deterioration of febrile neutropenia in the patient, said communication prompting the patient to perform at least one of: seeking professional medical care, and begin taking antibiotics.

In another embodiment, a method for home monitoring and detection of febrile neutropenia in a patient is provided that includes the steps of: sensing photoplethysmographic signals of the patient with a photoplethysmographic sensor worn by the patient; sensing blood borne parameters in the patient's blood with one or more blood borne parameter sensors; transmitting the sensed photoplethysmographic signals and blood borne parameters to a febrile neutropenia monitoring application; and determining, by the febrile neutropenia monitoring application, the presence or deterioration of febrile neutropenia based on the received information.

In one embodiment the method further comprises sensing movement of the patient with a wearable movement sensor; and correcting the photoplethysmographic signals based on information sensed by the movement sensor.

In another embodiment, the method comprises providing, by the febrile neutropenia monitoring application, an alarm to a healthcare provider computer upon a determination of the presence or deterioration of febrile neutropenia in the patient.

In yet another embodiment, the method further comprises providing, by the febrile neutropenia monitoring application, an alarm to a healthcare provider computer upon a determination of patient non-compliance with a patient monitoring protocol.

In still yet another embodiment, the method further comprises sensing the patient's body temperature with a temperature sensor, wherein the determining, by the febrile neutropenia monitoring application, of the presence or deterioration of febrile neutropenia is further based on the sensed temperature information.

In another embodiment, the method comprises sensing at least one of the patient's blood pressure and weight, wherein the determining, by the febrile neutropenia monitoring application, is further based on the at least one of a blood pressure and weight information.

In yet another embodiment, the method comprises determining, by the febrile neutropenia monitoring application, determine the patient's peripheral vascular resistance and heart rate based on the information sensed by the photoplethysmographic sensor.

In still yet another embodiment, the blood borne parameter sensors comprise a cell-based assay for sensing or counting at least one of neutrophils and monocytes.

In yet another embodiment, the blood borne parameter sensors comprise a multiplex biochemical assay for detecting at least one of: interleukin 1 and 6; tumor necrosis factor; procalcitonin; and C-reactive protein.

Yet another embodiment comprises providing, by the febrile neutropenia monitoring application, a communication to a patient computer, upon a determination of the presence or deterioration of febrile neutropenia in the patient, said communication prompting the patient to perform at least one of: seeking professional medical care, and begin taking antibiotics.

In yet another embodiment, a non-transitory computer readable medium is provided that contains instructions for home monitoring and detection of febrile neutropenia in a patient enabled at least in part on a processor of a computerized device, the instructions, which when executed by the processor, performing the steps of: receiving photoplethysmographic signals of the patient from a photoplethysmographic sensor worn by the patient; receiving blood borne parameters in the patient's blood from one or more blood borne parameter sensors; and determining the presence or deterioration of febrile neutropenia based on the information received from the photoplethysmographic sensor and the one or more blood borne parameter sensors.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 1 is a flow chart which schematically illustrates methods for evaluating whether a patient is suited for home monitoring for febrile neutropenia, in accordance with embodiments of the present disclosure.

DETAILED DESCRIPTION OF THE PRESENT INVENTION

Figure 2:
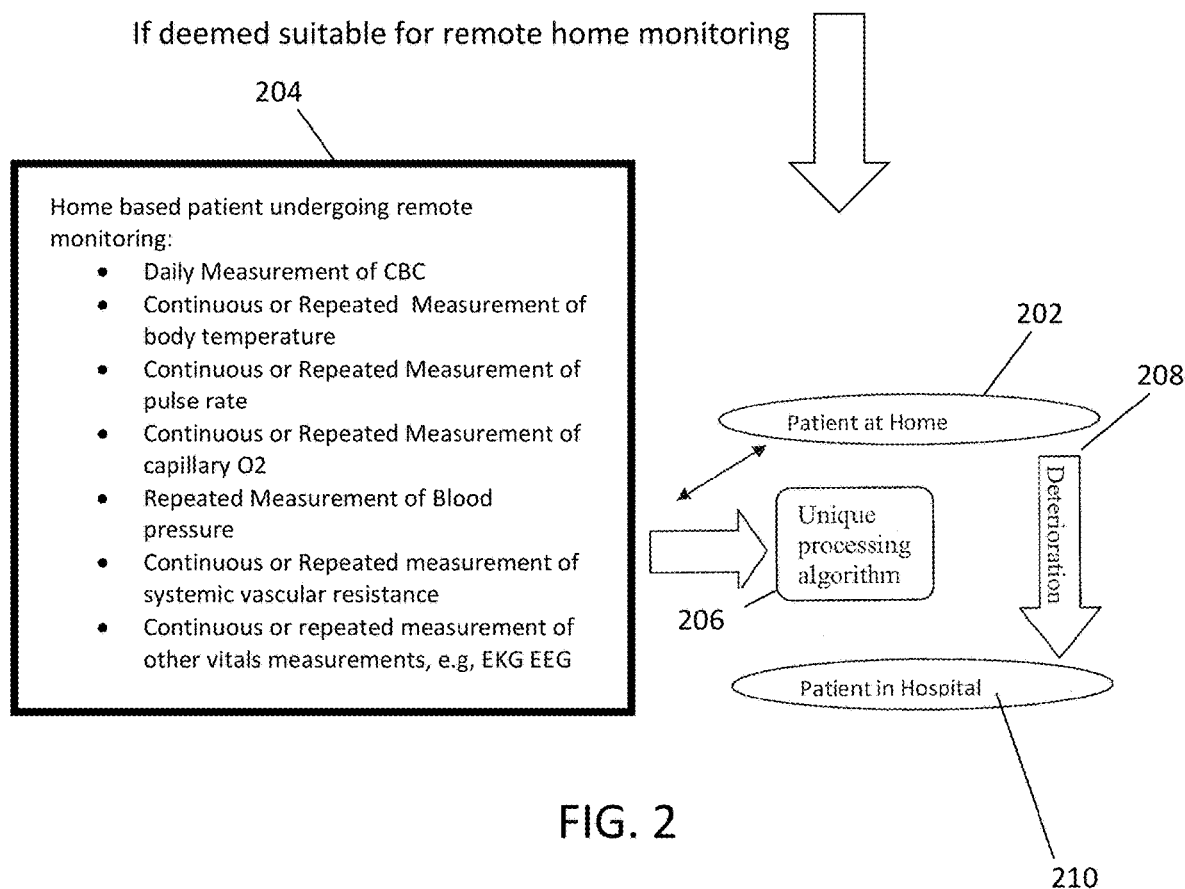
FIG. 2 is a flow chart which schematically illustrates a method for home monitoring and detection of febrile neutropenia in a patient, in accordance with embodiments of the present disclosure.

The present invention employs peripheral point-of-care devices, such as described herein, which allow for home monitoring of certain patient's vital statistics, combined with computer-executable instructions, including algorithms executed by a programmable computer.

Many embodiments of the present invention may take the form of computer-executable instructions, including algorithms executed by a programmable computer. However, the invention can be practiced with other computer system configurations as well. Certain aspects of the invention can be embodied in a special-purpose computer or data processor that is specifically programmed, configured or constructed to perform one or more of the computer-executable algorithms described below. Accordingly, the term "computer" as generally used herein refers to any data processor and includes Internet appliances, hand-held devices (including palm-top computers, wearable computers, cellular or mobile phones, multi-processor systems, processor-based or programmable consumer electronics, network computers, minicomputers) and the like.

The invention also can be practiced in distributed computing environments, where tasks or modules are performed by remote processing devices that are linked through a communications network. Moreover, the invention can be practiced in Internet-bases or cloud computing environments, where shared resources, software and information may be provided to computers and other devices on demand.

In a distributed computing environment, program modules or subroutines may be located in both local and remote memory storage devices. Aspects of the disclosure described below may be stored or distributed on computer-readable media, including magnetic and optically readable and removable computer disks, fixed magnetic disks, floppy disk drive, optical disk drive, magneto-optical disk drive, magnetic tape, hard-disk drive (HDD), solid state drive (SSD), compact flash or non-volatile memory, as well as distributed electronically over networks. Data structures and transmissions of data particular to aspects of the disclosure are also encompassed within the scope of the invention.

Neutropenic fever is defined by a physiology underlying the systemic inflammatory response syndrome (SIRS)[22] and sepsis. Hence, deterioration is clinically indicated by a deterioration of the physiologic parameters defining the SIRS, i.e. along with the cell count parameters (neutrophil/monocyte count) also the pulse rate, respiration rate and temperature. Further deterioration is then indicated by evidence of hypo-perfusion and organ dysfunction[22,23]. This is evidenced by blood pressure drop, decrease in cardiac output, change in peripheral vascular resistance and occasionally disseminated intravascular coagulation as well as mental status deterioration and decreased renal function.

Many, if not all, of the hallmarks of the SIRS and most clinical signs of early deterioration are accessible by currently available peripheral point of care devices (PPCD).

In some embodiments provided herein, parameters assessed include:
Blood count
Body temperature
Pulse rate
Capillary CO2 tension
Blood pressure/Systemic Vascular Resistance These physiologic parameters can be periodically or continuously measured on patients with neutropenic fevers. An integrated, unique algorithm signals early deterioration which ideally can be treated in the patient's home or the doctor's office before the deterioration becomes so severe as to lead to hospitalization.

FIG. 1 is a flowchart 100 illustrating methods for evaluating whether a patient is suited for home monitoring for medication induced febrile neutropenia, in accordance with an exemplary embodiment of the present disclosure. As shown at block 102, satisfaction of three initial criteria may be required before a further, initial assessment is performed on the patient. At block 104, an initial assessment is performed, which includes various assessments and/or analysis, including: a complete physical exam; CBS and CMP; urinalysis; lactic acid; microbiologic assessment; CXR if clinically indicated; and a risk assessment with MASCC score.

If results from the initial assessment indicate that the patient meets a low-risk MSACC score, further criteria may require satisfaction before deeming the patient suitable for remote home monitoring, as shown at block 106. Such criteria may include: the presence of a solid tumor; the patient lives within 1 hour (or some other suitable time/distance) of the treating center/physician; ability to tolerate oral medications and fluids; does not use PEG as route for nutrition; not currently on antibiotics; at least 18 years of age; and no quinolone allergy for oral regimens.

If it is determined that a patient is well-suited for home monitoring, e.g., after satisfaction of the evaluation as shown in FIG. 1, the patient may begin home monitoring for medication induced febrile neutropenia, as shown in FIG. 2. FIG. 2 is a flowchart 200 illustrating a method for home monitoring of a patient for medication induced febrile neutropenia, in accordance with embodiments provided by this disclosure.

As shown at 202, a patient's health parameters are monitored using one or more point-of-care monitoring devices. As shown at 204, monitored health parameters may include, for example: a daily measurement of complete blood count (CBC); continuous measurement of body temperature; continuous measurement of pulse rate; continuous measurement of capillary $O_2$; repeated measurement of blood pressure; and continuous measurement of systemic vascular resistance.

Various peripheral point-of-care devices exist for home monitoring of health parameters of a patient, and may be included in the systems and methods provided herein for home monitoring of a patient for medication induced febrile neutropenia. These include blood pressure monitors available from A & D and other vendors, blood glucose monitors available from MyClinicalHealth, Lifescan J & J and other vendors, thermometers available from Cardi Scientific and other vendors, pulse oximeters (pulse ox meters) available from Nonin and other vendors, peak flow monitors available from Microlife and other vendors, pedometers available from Omron and other vendors, and weight scales available from A & D Medical and other vendors. Many of these devices have been around for years. More recently point-of-care cell analyzers have been developed for blood cell counting and moving from the laboratory to home use. See "Integrated Systems for Rapid Point of Care (POC) Blood Cell Analysis" by vanBarkel et al, The Royal Society of Chemistry 2010, the entirety of which is incorporated herein by reference.

Many of the currently available monitors are fully automated and require no patient intervention. Others require simple prompting by the patient. Mass production of these monitors also has brought the cost of such monitors down significantly. By way of example Apple® and other smart watches include ECG capabilities as well as heart rate, blood pressure and blood oxygen monitoring and measurement capabilities. Several commercially available monitors include communication capabilities also for communicating with the computer either through hard wiring, or wirelessly. As the cost of computers also continues to fall, there presents an opportunity to reduce patient risks and costs, and at the same time improve patient outcome.

The health monitoring devices may be worn by the patient continuously while in an outpatient setting, such as at the patient's home, thereby providing continuous monitoring of the various health parameters. Alternatively, the patient may be prompted, e.g. by a timer or the like to periodically don the monitors for a reading. In order to ensure patient compliance, in an embodiment, one or more of the monitors may communicate, for example, wirelessly, to a central computer which would alert health care personnel if the patient fails to timely present his or herself for monitoring.

Information sensed by the healthcare monitoring devices may be processed by an algorithm, at 206, to determine a state of the patient's health, such as the presence of, or risk of developing, febrile neutropenia. The healthcare monitoring devices and/or a computer system running the algorithm may then provide an alert to health care personnel if the parameters assessed by the devices indicate clinical signs of early deterioration of the patient's health, at 208. Where early clinical signs of patient health deterioration are determined, the patient may be prompted to seek professional medical care (e.g., such as admission to a hospital, at 210) or to begin taking oral antibiotics which could be supplied to the patient ahead of time, or supplied, e.g. by a pharmacy, which may also be prompted by the system to dispense a course of antibiotics. Also, again to ensure patient compliance, the health care professional may be advised of a patient's health deterioration so that the health care professional could contact the patient if the patient does not make the contact first.

Figure 3:
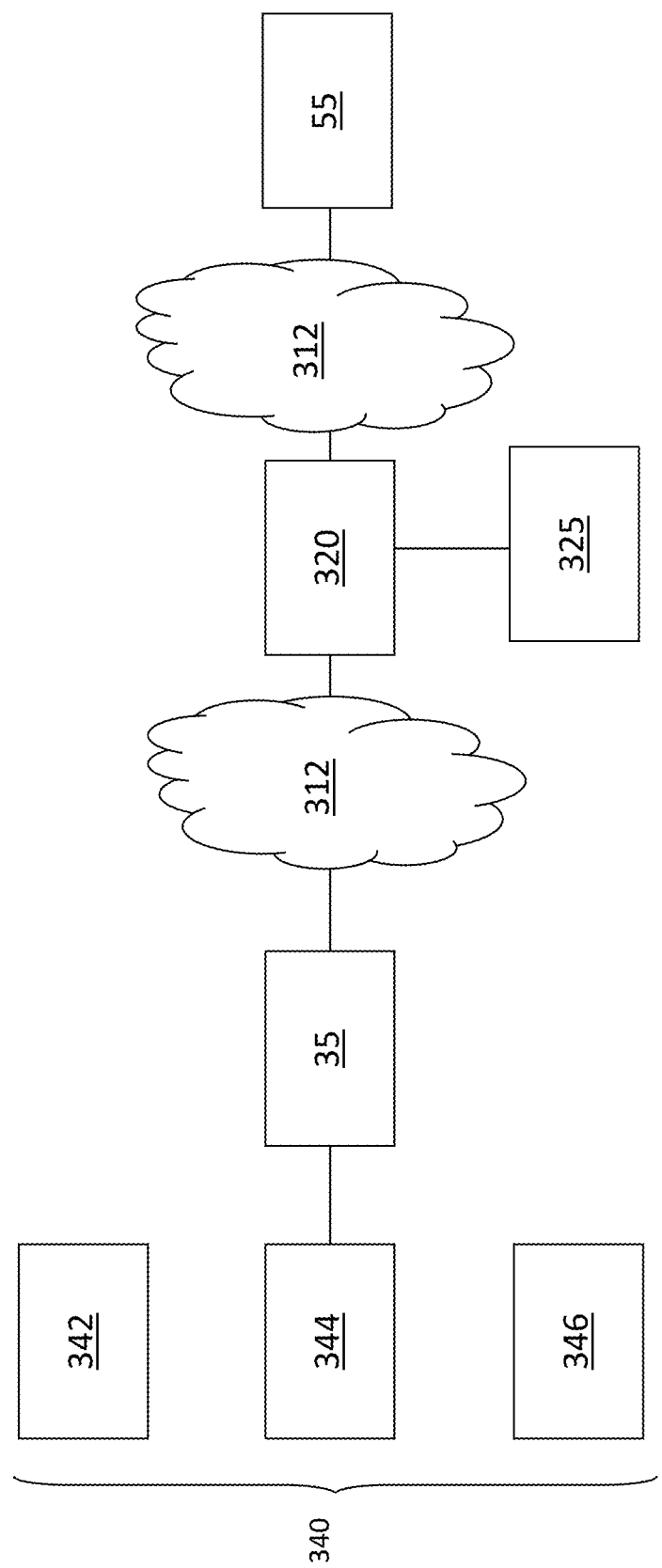
FIG. 3 is a schematic illustration of a system for home monitoring and detection of febrile neutropenia, in accordance with embodiments of the disclosure.

FIG. 3 is a schematic illustration of a system for home monitoring and detection of febrile neutropenia 30, in accordance with an exemplary embodiment of the present disclosure. The system for home monitoring and detection of febrile neutropenia 30, which may also be referred to as 'system 30', includes a febrile neutropenia monitoring application 325, which may be electronically accessible over at least one network system 312 and hosted at least partially on a server 320. A patient computer 35 is positioned to access the application 325, and a healthcare provider computer 55 may further be positioned to access the application 325. The system 30 further includes a variety of patient monitoring devices 340, which may include a photoplethysmographic sensor 342, movement sensor 344 and one or more blood borne parameter sensors 346.

The server 320 may be or include any database capable of storing and/or providing access to information, such as an electronic database, a computer and/or computerized server, database server or generally any network host capable of storing data and connected to any type of data network. Further, the server 320 may include or be a part of a distributed network or cloud computing environment. Any type of electronic and/or computerized device that is capable of storing information may be included as the server 320, and is considered within the scope of this disclosure. The server 320 may include computer-readable storage media, and a processor for processing data and executing algorithms, including any of the processes and algorithms set forth in this disclosure. The febrile neutropenia monitoring application 325 is electronically accessible over at least one network system 312. The network system 312 may include any type of network infrastructure, such as the Internet, or any other wired, wireless and/or partially wired network. The server 320, application 325 and network system 312 may include a variety of hardware and software components to provide successful functioning of the server 320 and the application 325, as is well-known within the art. Further, any features, characteristics, designs and/or functions that are known within the art may be included with the system 30 to further enhance its efficiency.

The patient computer 35 may be any computerized device that is capable of communicating with the application 325, for example via a network system 312, and may be operated by any patient for home monitoring of febrile neutropenia, or any representative thereof. Similarly, the healthcare provider computer 55 may be any computerized device that is capable of communicating with the application 325, for example via a network system 312, and may be operated by any physician, nurse or other healthcare provider, or any representative thereof. Any number of patient computers 35 and healthcare provider computers 55 may use the system 30 at any given time. The patient computer 35 and healthcare provider computer 55 may access the application 325 through a variety of ways, including through a computerized device in communication with the system 30 over a network system. For example, the patient computer 35 and/or healthcare provider computer 55 may be any computer, including any personal computer, Internet appliance, hand-held device (including palm-top computers, wearable computers, cellular or mobile phones, ipads, multi-processor systems, processor-based or programmable consumer electronics, network computers, minicomputers) and the like. One or more input devices, such as a keyboard or mouse, may be used to transmit information to and/or request information from the application 325 by the patient computer 35 and/or the healthcare provider computer 55.

The system 30 includes a plurality of point-of-care devices for monitoring or sensing parameters related to a patient's health (e.g., patient monitoring devices 340), which may be wearable monitoring devices that are operationally worn on the patient for measuring selected parameters as described herein. Readings from the patient monitoring devices 340 are transmitted to a computer (e.g., patient computer 35 and/or server 320) which includes or accesses the febrile neutropenia monitoring application 325 for monitoring and evaluating changes in the patient's vital statistics. The information sensed by the patient monitoring devices 340 may be transmitted directly to the server 320, or may be transmitted to the patient computer 35 (e.g., a patient's home-based computer, such as a laptop, desktop computer, smartphone or the like) which then communicates the sensed information to the application 325.

The febrile neutropenia monitoring application 325 may be fully or partially hosted on the server 320. Alternatively, the application 325 may be hosted and/or accessed on a patient's local computer, such as patient computer 35. The febrile neutropenia monitoring application 325 may include any tool, device, system, process or combination thereof, which assists or makes possible determining when a patient's measured parameters are approaching or are out of compliance with pre-determined criteria suggesting the onset or presence of febrile neutropenia, or deterioration of health in a patient with febrile neutropenia. The application 325 may include any computer-readable memory or databases, which may be stored in any computer-readable medium, and may be accessible by a computer processor. The application 325 may further include or access computer program instructions which may cause a processor to perform any algorithms and/or functions which may be described in this disclosure.

Further, the application 325 may provide access to a web or network-based platform, including a graphical user interface or webpage which provides interactive access to the system 30 to a user of a patient computer 35 and/or a healthcare provider computer 55. Alternatively or additionally, a patient computer 35 and/or healthcare provider computer 55 may include software providing access to the system 30.

The photoplethysmographic sensor 342 may be, for example, a wearable pulse oximeter. A wearable movement sensor 344 may be included to correct motion and/or gravitational interferences in the patient's photoplethysmographic signal. The patient's peripheral vascular resistance and the change in the peripheral vascular resistance may be determined from information sensed by the photoplethysmographic sensor 342. The patient's heart rate, an important vital parameter for the detection of febrile neutropenia and deterioration in febrile neutropenia, may be provided and/or determined (e.g., by the application 325) from the frequency of the photoplethysmographic signal. The patient's temperature may be recorded by a temperature sensor and transmitted to the application 325, as temperature may serve as a factor for the detection of febrile neutropenia and deterioration in febrile neutropenia. The patient monitoring devices 340 may further include a blood pressure sensor, such as a blood pressure cuff, and a scale for measuring the patient's weight. Additional patient monitoring devices 340 may be included for monitoring any health-related parameter which may be relevant to the determination of febrile neutropenia or deterioration of febrile neutropenia, including, for example, devices for monitoring or sensing any of the parameters listed at block 204 of FIG. 2.

Physiological parameters (e.g., as sensed by the photoplethysmographic sensor 342) may be correlated in real-time with blood borne parameters, such as sensed by blood borne parameter sensors 346. The blood borne parameter sensors 346 may include or utilize LFIRE (Label-Free Internal Reflection Ellipsometry) by Maven Technologies, LLC, as disclosed at least in part in one or more of the following U.S. Pat. Nos., each of which are incorporated in their entireties herein by reference: U.S. Pat. Nos. 6,594,011; 7,023,547; 6,859,280; 6,882,420; 7,002,686; 7,193,711; 7,518,724; 8,039,270; and 8,355,133.

The blood borne parameter sensors 346 may include cell-based assays for sensing or counting neutrophils and/or monocytes in a sample of the patient's blood, and may further include sensors for multiplex biochemical assays for simultaneous detection of binding events to nucleic acid or protein microarray on the sensor surface. Such multiplex biochemical assays may detect parameters relevant to a determination of febrile neutropenia or deterioration of febrile neutropenia such as: interleukin 1 and 6; tumor necrosis factor; procalcitonin; and C-reactive protein.

When neutropenia is suggested, the system 30 may raise an alarm prompting the patient or patient's caregiver to administer oral antibiotics and/or prompting the patient to seek medical care. For example, the application 325, upon determining that the information sensed by the patient monitoring devices 340 indicates the presence or deterioration of febrile neutropenia, may initiate an alarm or other communication to be transmitted to a healthcare provider computer 55.

By sensing and recording changes in a patient's selected parameters, early intervention, e.g. through administration of oral antibiotics may be prescribed. As a result, hospitalization of the patient may be avoided.

In a survey study, which was initially presented at the yearly ASCO meeting in 2004, 82% of physicians have claimed to treat some or all of their low-risk febrile neutropenic patients as outpatients while 17% exclusively used inpatient treatment[24]. Despite existing guidelines, 18 only one third of the responding physicians complied with the evidence based pattern of care[24]. Similar observation has been reported from studies in Canada and the UK, with the lowest acceptance towards outpatient treatment in low risk patients being observed in Europe[25,26].

Elting presented a retrospective analysis of 712 patients[27], who were prospectively treated on the University of Texas MD Anderson Cancer Center low-risk neutropenic fever algorithm pathway[15 28]. The patients, who were treated as outpatients were compared to a small subset of patients who were on clinical assessment candidates for the outpatient pathway, but were deemed on the grounds of psychosocial criteria, such as absence of access to caregivers at home, no telephone or no transportation in case of emergency or a history of non-compliance with other outpatient regimens not to be eligible for treatment as outpatients. Treatment as outpatient was in average associated with savings of 7.432$ in costs per neutropenic fever episode (15.231,$ vs 7.799$)[27].

Hendricks[19] evaluated the differences in costs between the in- and out-patient population in Talcott's randomized controlled trial[11]. This analysis included all financial aspects incurred by a patient with acute febrile neutropenic fever episode, including along with billing information from hospitals, outpatient clinicians and home care providers also indirect costs such as informal caregivers' time expense (family labor)[19]. Again, a striking difference between charges for the hospital vs home based care were observed with 15.495$ vs 7.868$. Even including indirect costs, such as opportunity costs for family members, the difference still remained highly significant 16.341$ vs 10.977$ (P<0.0 1), with basically identical clinical complication rates.

Teuffel's cost effectiveness analysis in the context of the Canadian health system[20] compared four different approaches, entire in hospital management with IV antibiotics until neutrophil recovery (HospIV), early discharge after a limited course of in hospital IV antibiotics, followed by home PO antibiotics (EarlyDC), entire outpatient management with IV antibiotics (HomeIV) and entire outpatient management with PO antibiotics (HomePO). The mean costs for the different approaches were 13.557 C$, 6.15 C$, 4.83 C$ and 3.470 C$, reflecting a significant cost savings in each of the outpatient based treatment paradigms. The corresponding probabilistic willingness-to-pay analysis, which used a Canadian standard of 4.000 C$ for quality of life adjusted febrile neutropenia episode, revealed cost effective results in 1% HospIV, 8% EarlyDC 38% HomeIV and 54% HomePO of all simulated outcomes, respectively[20].

Various other physiologic parameters or markers may be monitored and evaluated, including but not limited to:

Markers:
1. Continuously measured electrocardiographic parameters (may also be more accurately measured repeatedly using separate, 6 lead electrocardiograph):
   1. Three classes of heartbeats:
      a. normal beat
      b. ventricular beat, including:
         i. premature ventricular contraction
         ii. ventricular escape beat
      c. supraventricular beat, including:
         i. aberrated atrial premature beat
         ii. nodal (junctional) premature beat
         iii. atrial premature contraction
         iv. nodal (junctional) escape beat
         v. atrial escape beat.
   2. Rhythms:
      a. normal sinus rhythm
      b. sinus bradycardia
      c. sinus tachycardia
      d. supraventricular rhythm
      e. atrial bigeminy
      f. atrial trigeminy
      g. atrial fibrillation
      h. atrial flutter
      i. supraventricular tachycardia
      j. supraventricular couplet
      k. idioventricular rhythm
      l. ventricular bigeminy
      m. ventricular trigeminy
      n. ventricular fibrillation
      o. ventricular flutter
      p. ventricular bradycardia
      q. ventricular tachycardia
      r. ventricular couplet.
   3. Heart rate variability analysis:
      a. time-domain methods (AVNN, VARNN, SDNN, SDANN, RMSSD, SDSD, NN50, pNN50)
      b. geometric methods (NN histogram, HRV triangular index)
      c. frequency-domain methods (LF, HF)
      d. non-linear methods (detrended fluctuation analysis, entropy analysis)

Other Markers:
1. Continuous electroencephalography
   a. Relative power and coherence of frequency bands measuring
      i. Delta waves (<4 Hz)
      ii. Theta waves (≥4 Hz and <8 Hz)
      iii. Alpha waves (≥8 Hz and <14 Hz in posterior regions of head)
      iv. Beta waves (≥14 Hz and <32 Hz)
      v. Gamma waves (≥32 Hz)
      vi. Mu waves (≥8 Hz and <12 Hz in sensorimotor cortex)
2. Continuous beat-to-beat blood pressure (distinct from repeated blood pressure measurement)
3. Repeated spirometer measurement
   a. Spirometric values
      i. FVC—Forced vital capacity; the total volume of air that can be exhaled during a maximal forced expiration effort.
      ii. FEV1—Forced expiratory volume in one second; the volume of air exhaled in the first second under force after a maximal inhalation.
      iii. FEV1/FVC ratio—The percentage of the FVC expired in one second.
      iv. FEV6—Forced expiratory volume in six seconds.
      v. FEF25-75%—Forced expiratory flow over the middle one half of the FVC; the average flow from the point at which 25 percent of the FVC has been exhaled to the point at which 75 percent of the FVC has been exhaled.
      vi. MVV—Maximal voluntary ventilation.
   b. Lung volumes
      i. ERV—Expiratory reserve volume; the maximal volume of air exhaled from end-expiration.
      ii. IRV—Inspiratory reserve volume; the maximal volume of air inhaled from end-inspiration.
      iii. RV—Residual volume; the volume of air remaining in the lungs after a maximal exhalation.
      iv. VT—Tidal volume; the volume of air inhaled or exhaled during each respiratory cycle.
   c. Lung capacities
      i. FRC—Functional residual capacity; the volume of air in the lungs at resting end-expiration.
      ii. IC—Inspiratory capacity; the maximal volume of air that can be inhaled from the resting expiratory level.
      iii. TLC—Total lung capacity; the volume of air in the lungs at maximal inflation.
      iv. VC—Vital capacity; the largest volume measured on complete exhalation after full inspiration.
4. Continuous measurement of temperature parameters
   a. temperature trajectory measured from an initial point (the temperature value at some time defined as 0) and form (shape defined by a mathematical function), as well as rate of change (speed), and change in rate (acceleration)
   b. Standard deviation of temperature
   c. temperature differential calculated between multiple continuous measurements taken by wearable sensors
5. Continuous measurement of respiratory rate via wearable accelerometer
6. Repeated lactate measurement via blood gas analysis devices equipped with a lactate measuring electrode 7. Repeated measurement of cytokine interleukin-3 (IL-3) levels in blood plasma
8. Repeated procalcitonin (PCT) measurement
9. Repeated measurement of circulating tumor cells (CTC)

Additional Indications/Effects Detected:
Cytokine release storm
Sepsis
Pneumonitis
Acute pulmonary toxicity
Cardiac toxicities
Gastric toxicities
Neurotoxicity All of the above indications/effects may be monitored and measured on an out-patient basis using wearables, or portable in-home use devices such as weight scales, spirometers, or simple automated blood or saliva, etc., testers, which are configured to report readings directly or indirectly to a patient computer.

It should be emphasized that the above-described embodiments of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention.

All such modifications and variations are intended to be included herein within the scope of this invention and the present invention and protected by the following claims.

REFERENCES

Each of the following references are incorporated in their entireties herein, by reference:
1. Freifeld, A. G. et al. Clinical practice guideline for the use of antimicrobial agents in neutropenic patients with cancer: 2010 update by the infectious diseases society of America. *Clinical infectious diseases: an official publication of the Infectious Diseases Society of America* 52, e56-93 (2011).
2. Teuffel, O., Ethier, M C., Alibhai, S. M. H., Beyene, J. & Sung, L. Outpatient management of cancer patients with febrile neutropenia: a systematic review and meta-analysis. *Annals of oncology: official journal of the European Society for Medical Oncology/ESAJO* 22, 2358-65 (2011).
3. Bodey, G. P., Buckley, M., Sathe, Y. S. & Freireich, E. J. Quantitative relationships between circulating leukocytes and infection in patients with acute leukemia. *Annals of internal medicine* 64, 328-40 (1966).
4. Klastersky, J. et al. The Multinational Association for Supportive Care in Cancer risk index: A multinational scoring system for identifying low-risk febrile neutropenic cancer patients. *Journal of clinical oncology: official journal of the American Society of Clinical Oncology* 18, 3038-51 (2000).
5. Hidalgo, M. et al. Outpatient therapy with oral ofloxacin for patients with low risk neutropenia and fever: a prospective, randomized clinical trial. *Cancer* 85, 2 13-9 (1999).
6. Malik, I. A., Khan, W. A., Karim, M., Aziz, Z. & Khan, M. A. Feasibility of outpatient management of fever in cancer patients with low-risk neutropenia: results of a prospective randomized trial. *The American journal of medicine* 98, 224-31 (1995).
7. Rapoport, B. L. et al. Ceftriaxone plus once daily aminoglycoside with filgrastim for treatment of febrile neutropenia: early hospital discharge vs. Standard In-patient care. *Chemotherapy* 45, 466-76
8. Innes, H. E. et al. Oral antibiotics with early hospital discharge compared with in-patient intravenous antibiotics for low-risk febrile neutropenia in patients with cancer: a prospective randomised controlled single centre study. *British journal of cancer* 89, 43-9 (2003).
9. Santolaya, M. E. et al. Early hospital discharge followed by outpatient management versus continued hospitalization of children with cancer, fever, and neutropenia at low risk for invasive bacterial infection. *Journal of clinical oncology: official journal of the American Society of Clinical Oncology* 22, 3784-9 (2004).
10. Ahmed, N. et al. Early hospital discharge versus continued hospitalization in febrile pediatric cancer patients with prolonged neutropenia: A randomized, prospective study. *Pediatric blood & cancer* 49, 786-92 (2007).
11. Talcott, J. A. et al. Safety of early discharge for low-risk patients with febrile neutropenia: a multicenter randomized controlled trial. *Journal of clinical oncology: official journal of the American Society of Clinical Oncology* 29, 3 977-83 (2011).
12. Gupta, A., Swaroop, C., Agarwala, S., Pandey, R. M. & Bakhshi, S. Randomized controlled trial comparing oral amoxicillin-clavulanate and ofloxacin with intravenous ceftriaxone and amikacin as outpatient therapy in pediatric low-risk febrile neutropenia. *Journal of pediatric hematology/oncology* 31, 635-41(2009).
13. Minotti, V. et al. Domiciliary treatment of febrile episodes in cancer patients: a prospective randomized trial comparing oral versus parenteral empirical antibiotic treatment. *Supportive care in cancer: official journal of the Multinational Association of Supportive Care in Cancer* 7, 134-9 (1999).
14. Sebban, C. et al. Oral moxifloxacin or intravenous ceftriaxone for the treatment of low-risk neutropenic fever in cancer patients suitable for early hospital discharge. *Supportive care in cancer: official journal of the Multinational Association of Supportive Care in Cancer* 16, 10 17-23 (2008).
15. Rubenstein, E. B. et al. Outpatient treatment of febrile episodes in low-risk neutropenic patients with cancer. *Cancer* 71, 3640-6 (1993).
16. Segal, B. H. et al. Prevention and treatment of cancer-related infections. *Journal of the National Comprehensive Cancer Network: JNCCN* 6, 122-74 (2008).
17. Jun, H. X. et al. Clinical guidelines for the management of cancer patients with neutropenia and unexplained fever. *International journal of antimicrobial agents* 26 Suppl 2, S 128-32; discussion S 133-40 (2005).
18. Hughes, W. T. et al. 2002 guidelines for the use of antimicrobial agents in neutropenic patients with cancer. *Clinical infectious diseases: an official publication of the Infectious Diseases Society of America* 34, 730-51 (2002).
19. Hendricks, A. M., Loggers, E. T. & Talcott, J. A. Costs of home versus inpatient treatment for fever and neutropenia: analysis of a multicenter randomized trial. *Journal of clinical oncology: official journal of the American Society of Clinical Oncology* 29, 3984-9 (2011).
20. Teuffel, O., Amir, E., Alibhai, S., Beyene, J. & Sung, L. Cost effectiveness of outpatient treatment for febrile neutropaenia in adult cancer patients. *British journal of cancer* 104, 1377-83(2011).

21. National Comprehensive Cancer Network (NCCN) Clinical Practice Guidelines in Oncology. Prevention and treatment of cancer-related infections. http://www.nccn.org (2011).
22. Levy, M. M. et al. 2001 SCCM/ESICM/ACCP/ATS/SIS International Sepsis Definitions Conference. *Critical care medicine* 31, 125 0-6 (2003).
23. Annane, D., Bellissant, F. & Cavaillon, J. M. Septic shock. *Lancet* 365, 63-78
24. Freifeld, A., Sankaranarayanan, J., Ullrich, F. & Sun, J. Clinical practice patterns of managing low-risk adult febrile neutropenia during cancer chemotherapy in the USA. *Supportive care in cancer: official journal of the Multinational Association of Supportive Care in Cancer* 16, 18 1-91 (2008).
25. Innes, H., Billingham, L., Gaunt, C., Steven, N. & Marshall, E. Management of febrile neutropenia in the United Kingdom: time for a national trial? *British journal of cancer* 93, 1324-8 (2005).
26. Sung, L. et al. Inpatient versus outpatient management of low-risk pediatric febrile neutropenia: measuring parents' and healthcare professionals' preferences. *Journal of clinical oncology: official journal of the American Society of Clinical Oncology* 22, 3922-9 (2004).
27. Elting, L. S. et al. Outcomes and cost of outpatient or inpatient management of 712 patients with febrile neutropenia. *Journal of clinical oncology: official journal of the American Society of Clinical Oncology* 26, 606-11 (2008).
28. Escalante, C. P. et al. Outcomes of treatment pathways in outpatient treatment of low risk febrile neutropenic cancer patients. *Supportive care in cancer: official journal of the Multinational Association of Supportive Care in Cancer* 12, 657-62 (2004).

The invention claimed is:

1. A system for out-patient, home monitoring and detection of chemotherapy induced adverse side effects in a patient, the system comprising:
   one or more patient physical parameters sensors selected from:
   a temperature sensor for sensing patient temperature;
   a pulse oximeter for sensing photoplethysmographic signals of the patient;
   a movement sensor for sensing movement of the patient and for correcting for motion and/or gravitational interferences in the patient's photolethysmographic signals resulting from said sensed movements;
   a breathing sensor for sensing patient breathing rate, breathing depth and lung volume;
   a heart monitor for sensing heart rate, blood pressure, blood oxygen level and/or electrocardiogram functions;
   one or more point-of-care blood borne parameter sensors for sensing parameters in the patient's blood including neutrophil count; and
   a weight scale for measuring the patient's weight;
   wherein the one or more patient physical parameter sensors are hosted at least partially on a server and electronically accessible over at least one network system to a patient computer,
   wherein the home monitoring and detection system is configured to determine the patient's peripheral vascular resistance and heart rate based on information sensed by the pulse oximeter, and/or to receive information sensed by the temperature sensor, and/or the one or more blood borne parameter sensors, and/or the weight scale, the heart monitor, the patient breathing sensor, the movement sensor and the one or more point-of-care blood borne parameter sensors, and to determine, based on the received information, a change in the patient's condition, and should said change approach or be out of compliance with pre-determined criteria, indicative of the possible presence or deterioration of chemotherapy induced adverse side effects in the patient, provide an alarm to a healthcare provider and/or the patient upon a determination of the presence of or deterioration of patient physical parameters in a patient.

2. The system of claim 1 further comprising a healthcare provider computer located remotely from the patient's home, wherein the temperature sensor is configured to provide an alarm to the healthcare provider computer upon a determination of a fever temperature of the patient.

3. The system of claim 2, wherein the system is configured to provide an alarm to the healthcare provider computer upon a determination of patient non-compliance with a patient monitoring protocol.

4. The system of claim 1, further comprising a blood pressure sensor,
   wherein the system is configured to receive information sensed by the blood pressure sensor and to determine the presence or deterioration of the patient's health condition based at least in part on the information sensed by the blood pressure sensor.

5. The system of claim 1, wherein the blood borne parameter sensors comprise a cell-based assay for sensing or counting monocytes.

6. The system of claim 1, wherein the temperature sensor is configured to provide an alarm to the patient computer, upon a determination of the presence a fever temperature of the patient, said alarm prompting the patient to perform at least one of: seeking professional medical care, and begin taking antibiotics.

7. The system of claim 1, wherein the heart monitor comprises a smart watch.

8. The system of claim 1, wherein the chemotherapy induced adverse side effects are cancer treatment related adverse side effects.

9. A method for out-patient home monitoring and detection of chemotherapy induced adverse side effects in a patient, the method comprising:
   sensing one or more of the following patient physical parameters:
   the patient's body temperature with a temperature sensor;
   sensing photoplethysmographic signals of the patient including vascular resistance, heart rate and blood oxygen saturation with a pulse oximeter;
   sensing patient breathing rate, breathing depth and/or lung volume;
   sensing movement of the patient and correcting for motion and/or gravitational interferences of the patient's photoplethysmographic signals resulting from said sensed movement;
   sensing heart rate, blood pressure, blood oxygen level and/or electrocardiogram functions;
   sensing the patient's weight with a scale;
   sensing blood borne parameters in the patient's blood, including neutrophil count, with one or more point-of-care blood borne parameter sensors;
   transmitting the sensed parameter(s) to a patient physical parameter monitoring application;
   determining, based on changes in the sensed patient physical parameter(s), if said signals are approaching or out of compliance with pre-determined criteria, indicative of the presence or deterioration of chemotherapy induced adverse side effects; and providing an alarm to a healthcare provider and/or the patient upon a determination of the presence of or deterioration of patient physical parameters in a patient.

10. The method of claim 9, further comprising:
providing, by the temperature sensor, an alarm to a healthcare provider computer located remotely from the patient's home upon a determination of the presence or deterioration of febrile neutropenia in the patient.

11. The method of claim 9, further comprising:
providing, by the temperature sensor, an alarm to a healthcare provider computer upon a determination of a fever temperature of the patient.

12. The method of claim 9, further comprising:
sensing the patient's blood pressure, wherein a change in the patient's health condition is determined based on changes in the blood pressure information.

13. The method of claim 9, wherein the blood borne parameter sensors comprise a cell-based assay for sensing or counting at least one of neutrophils and monocytes.

14. The method of claim 9, further comprising:
providing, by the temperature sensor, an alarm to a patient computer, upon a determination of a fever temperature of the patient, said alarm prompting the patient to perform at least one of: seeking professional medical care and begin taking antibiotics.

15. The method of claim 9, wherein the chemotherapy induced adverse side effects are cancer treatment related adverse side effects.

16. A non-transitory computer readable medium containing instructions for home monitoring and detection of chemotherapy induced adverse side effects in a patient enabled at least in part on a processor of a computerized device, the instructions, which when executed by the processor, performing the steps of:
receiving readings of one or more patient physical parameters including:
receiving body temperature readings of the patient;
receiving photoplethysmographic signals of the patient including vascular resistance, heart rate and blood oxygen saturation from a pulse oximeter;
receiving correction signals for the photoplethysmographic signals based on sensed movement of the patient;
receiving heart rate, blood pressure, blood oxygen level and/or electrocardiogram function signals of the patient;
receiving patient body weight signals from a scale;
receiving blood borne parameters including neutrophil count in the patient's blood from one or more point-of-care blood borne parameter sensors;
receiving patient breathing rate, breathing depth and/or lung volume signals;
determining if said readings are approaching or out of compliance with pre-determined conditions, indicative of the presence or deterioration of chemotherapy induced adverse side effects based on changes in the signals received from the sensor(s); and
providing an alarm to a healthcare provider and/or the patient upon a determination of the presence or deterioration of chemotherapy induced adverse side effects in the patient.

17. The non-transitory computer readable medium of claim 16, wherein the chemotherapy induced adverse side effects are cancer treatment related adverse side effects.

* * * * *